US012651657B2

(12) United States Patent

Neumann

(10) Patent No.: US 12,651,657 B2

(45) Date of Patent: Jun. 9, 2026

(54) SYSTEMS AND METHODS FOR INITIATING AN UPDATED USER AMELIORATIVE PLAN

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 1090 days.

(21) Appl. No.: 17/493,064

(22) Filed: Oct. 4, 2021

(65) Prior Publication Data

US 2022/0028511 A1     Jan. 27, 2022

Related U.S. Application Data

(63) Continuation-in-part of application No. 16/668,369, filed on Oct. 30, 2019, now Pat. No. 11,170,315.

(51) Int. Cl.
G16H 20/00      (2018.01)
G06N 20/00      (2019.01)

(52) U.S. Cl.
CPC ............. G16H 20/00 (2018.01); G06N 20/00 (2019.01)

(58) Field of Classification Search
CPC .............................. G16H 20/00; G06N 20/00
See application file for complete search history.

(56) References Cited

U.S. PATENT DOCUMENTS

| | | | |
|---|---|---|---|
| 8,684,922 B2 | 4/2014 | Tran | |
| 9,719,147 B1 | 8/2017 | Fernandez | |
| 11,170,315 B2 * | 11/2021 | Neumann | G06F 16/285 |
| 2004/0199482 A1 * | 10/2004 | Wilson | G16H 50/20 |
| | | | 706/924 |
| 2007/0293370 A1 * | 12/2007 | Klingler | A63B 24/00 |
| | | | 482/4 |
| 2015/0161331 A1 | 6/2015 | Oleynik | |
| 2015/0364026 A1 * | 12/2015 | Rubin | G06Q 10/063114 |
| | | | 340/539.11 |

(Continued)

FOREIGN PATENT DOCUMENTS

| | | | |
|---|---|---|---|
| WO | WO-2017031319 A1 * | 2/2017 | ........... A61K 31/475 |
| WO | 2019055336 | 3/2019 | |

OTHER PUBLICATIONS

Levine et al. (Variations in Patterns of Highly Active Antiretroviral Therapy (HAART) Adherence, Aug. 2005, pp. 355-362) (Year: 2005).*

(Continued)

*Primary Examiner* — George Giroux
(74) *Attorney, Agent, or Firm* — Caldwell LLC

(57)     ABSTRACT

A system for initiating an updated user ameliorative plan includes a processor configured to identify a user ameliorative plan as a function of a user identifier from a user client device, obtain a periodic longevity factor, determine a user adherence factor, wherein determining further comprises identifying a progression locus as a function of the user ameliorative plan and the periodic longevity factor, receiving a user response, and determining the user adherence factor as a function of the progression locus and the adherence correlator, generate an updated user ameliorative plan as a function of the user adherence factor, and initiate the updated user ameliorative plan.

18 Claims, 11 Drawing Sheets

(56)                References Cited

U.S. PATENT DOCUMENTS

| | | | | |
|---|---|---|---|---|
| 2016/0321414 A1* | 11/2016 | Salganicoff | ............ | G06N 20/00 |
| 2017/0132396 A1* | 5/2017 | Bechtold | ................ | G16H 50/20 |
| 2017/0249434 A1 | 8/2017 | Brunner | | |
| 2017/0357760 A1 | 12/2017 | Han et al. | | |
| 2018/0089385 A1* | 3/2018 | Gupta | .................... | G16H 70/60 |
| 2018/0314805 A1* | 11/2018 | Chang | .................... | G16H 20/70 |
| 2018/0325385 A1 | 11/2018 | Deterding et al. | | |
| 2019/0019573 A1 | 1/2019 | Lake et al. | | |
| 2019/0088366 A1 | 3/2019 | Vaughan et al. | | |
| 2019/0115097 A1 | 4/2019 | Macoviak et al. | | |
| 2019/0371450 A1* | 12/2019 | Lou | ........................ | G16H 50/30 |
| 2019/0392924 A1* | 12/2019 | Bettencourt-Silva | ........................ | |
| | | | | G16H 50/70 |
| 2020/0005928 A1* | 1/2020 | Daniel | ................... | G16H 15/00 |

OTHER PUBLICATIONS

Srinivas et al. (Application of Data Mining Techniques in Healthcare and Prediction of Heart Attacks, Mar. 2010, pp. 250-255) (Year: 2010).*
Sweeney et al. (Artifact Removal in Physiological Signals—Practices and Possibilities, May 2012, pp. 488-500) (Year: 2012).*
Angelova et al. (Pruning Training Sets for Learning of Object Categories, 2005, pp. 1-8) (Year: 2005).*
Boursalie, Omar, Reza Samavi, and Thomas E. Doyle. "M4CVD: Mobile machine learning model for monitoring cardiovascular disease." Procedia Computer Science 63 (2015): 384-391.Retrieved on Oct. 8, 2019 from https://core.ac.uk/download/pdf/81989261. pdf.
Adeola, Ephraim, et al. "Using Wearable Biometric Devices to Improve Patient Healthcare Outcomes with Machine Learning Algorithms." Retrieved on Oct. 8, 2019 from http://csis.pace.edu/ ~ctappert/srd2017/2017PDF/d1.pdf.

* cited by examiner

100 —

400

User Database 128

| User Demographic Table 404 | User Identifier Table 408 | User Periodic Longevity Data Table 412 |

| User Adherence Data Table 416 | User Ameliorative Plan 420 | Expert Link Table 424 |

800

Ameliorative Training Set Database 188

Periodic Longevity Classification Table 804

Cluster Adherence Table 808

Ameliorative Table 812

Ameliorative Model Table 816

Expert Link Table 820

SYSTEMS AND METHODS FOR INITIATING AN UPDATED USER AMELIORATIVE PLAN

CROSS-REFERENCE TO RELATED APPLICATIONS

This application is a continuation-in-part of Non-provisional application Ser. No. 16/668,369 filed on Oct. 30, 2019 and entitled "METHODS AND SYSTEMS FOR PROVIDING DYNAMIC CONSTITUTIONAL GUIDANCE," the entirety of which is incorporated herein by reference.

FIELD OF THE INVENTION

The present invention generally relates to the field of artificial intelligence. In particular, the present invention is directed to methods and systems for initiating an updated user ameliorative plan.

BACKGROUND

Accurate constitutional guidance can be challenging to implement due to the dynamic variances in a user's constitution on a daily basis. Further, understanding a user's own adherence can be challenging to interpret, creating further complexities.

SUMMARY OF THE DISCLOSURE

In an aspect, a system for initiating an updated user ameliorative plan includes a processor configured to identify a user ameliorative plan as a function of a user identifier from a user client device, obtain a periodic longevity factor, determine a user adherence factor, wherein determining further comprises identifying a progression locus as a function of the user ameliorative plan and the periodic longevity factor, receiving a user response, and determining the user adherence factor as a function of the progression locus and the adherence correlator, generate an updated user ameliorative plan as a function of the user adherence factor, and initiate the updated user ameliorative plan.

In an aspect, a method a for initiating an updated user ameliorative plan includes identifying, by a processor, a user ameliorative plan as a function of a user identifier from a user client device, obtaining, by the processor, a periodic longevity factor, determining, by the processor, a user adherence factor, wherein determining further comprises identifying a progression locus as a function of the user ameliorative plan and the periodic longevity factor, receiving a user response, and determining the user adherence factor as a function of the progression locus and the adherence correlator, generating, by the processor, an updated user ameliorative plan as a function of the user adherence factor, and initiating, by the processor, the updated user ameliorative plan.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Figure 1:
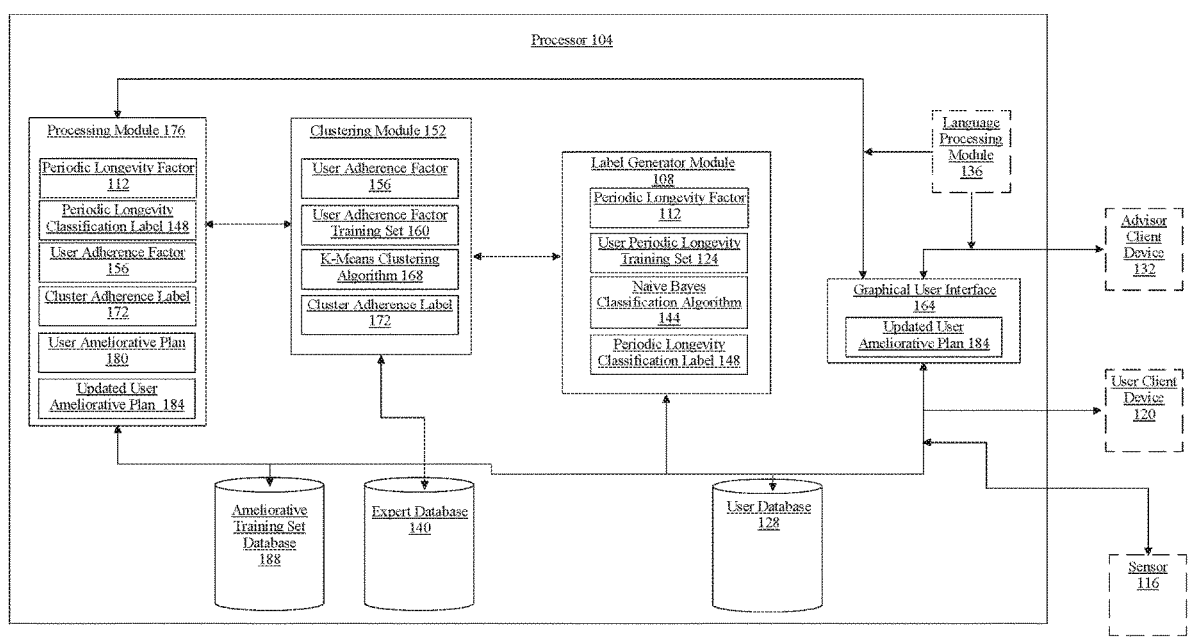
FIG. 1 is a block diagram illustrating an exemplary embodiment of a system for providing dynamic constitutional guidance.

Referring now to the drawings, FIG. 1 illustrates an exemplary embodiment of a system 100 for providing dynamic constitutional guidance. System 100 includes a processor. A processor 104 may include any computing device as described herein, including without limitation a microcontroller, microprocessor, digital signal processor 104 (DSP) and/or system on a chip (SoC) as described herein. A processor 104 may be housed with, may be incorporated in, or may incorporate one or more sensor of at least a sensor. Computing device may include, be included in, and/or communicate with a mobile device such as a mobile telephone or smartphone. A processor 104 may include a single computing device operating independently, or may include two or more computing device operating in concert, in parallel, sequentially or the like; two or more computing devices may be included together in a single computing device or in two or more computing devices. A processor 104 with one or more additional devices as described below in further detail via a network interface device. Network interface device may be utilized for connecting a processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. A processor 104 may include but is not limited to, for example, A processor 104 or cluster of computing devices in a first location and a second computing device or cluster of computing devices in a second location. A processor 104 may include one or more computing devices dedicated to data storage, security, distribution of traffic for load balancing, and the like. A processor 104 may distribute one or more computing tasks as described below across a plurality of computing devices of computing device, which may operate in parallel, in series, redundantly, or in any other manner used for distribution of tasks or memory between computing devices. A processor 104 may be implemented using a "shared nothing" architecture in which data is cached at the worker, in an embodiment, this may enable scalability of system 100 and/or computing device.

With continued reference to FIG. 1, a processor 104 may be designed and/or configured to perform any method, method step, or sequence of method steps in any embodiment described in this disclosure, in any order and with any degree of repetition. For instance, a processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A processor 104 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a label generator module 108 operating on a processor. Label generator module 108 may be implemented as any hardware and/or software module. Label generator module 108 is designed and configured to receive a periodic longevity factor containing a user identifier from a user client device; retrieve a user periodic longevity factor training set from a user database as a function of the user identifier wherein the user periodic longevity factor training set contains a plurality of user data entries containing user periodic longevity data containing periodic longevity classification label; and generate a naïve Bayes classification algorithm utilizing the user periodic longevity factor training set wherein the naïve Bayes classification algorithm utilizes the periodic longevity factor as an input and outputs a periodic longevity classification label.

With continued reference to FIG. 1, a "periodic longevity factor" as used in this disclosure includes any health measurement of a user's body. A health measurement may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a health measurement may include at least a genetic sample. At least a genetic sample may include a complete genome of a person or any portion thereof. At least a genetic sample may include a DNA sample and/or an RNA sample. At least a health measurement may include an epigenetic sample, a proteomic sample, a tissue sample, a biopsy, and/or any other physically extracted sample. At least a health measurement may include an endocrinal sample. As a further non-limiting example, the at least a health measurement may include a signal from at least a sensor 116 configured to detect physiological data of a user and recording the at least a health measurement as a function of the signal. At least a sensor 116 may include any medical sensor 116 and/or medical device configured to capture sensor 116 data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor 116 may include any electromagnetic sensor 116, including without limitation electroencephalographic sensor 116, magnetoencephalographic sensor 116, electrocardiographic sensor 116, electromyographic sensor 116, or the like. At least a sensor 116 may include a temperature sensor 116. At least a sensor 116 may include any sensor 116 that may be included in a mobile device and/or wearable device, including without limitation a motion sensor 116 such as an inertial measurement unit (IMU), one or more accelerometers, one or more gyroscopes, one or more magnetometers, or the like. At least a wearable and/or mobile device sensor 116 may capture step, gait, and/or other mobility data, as well as data describing activity levels and/or physical fitness. At least a wearable and/or mobile device sensor 116 may detect heart rate or the like. At least a sensor 116 may detect any hematological parameter including blood oxygen level, pulse rate, heart rate, pulse rhythm, blood sugar, and/or blood pressure. At least a sensor 116 may be configured to detect internal and/or external biomarkers and/or readings. At least a sensor 116 may be configured to detect sleep cycles including sleep or wake cycles and times a user remains in each sleep or wake cycle, rapid eye movement sleep (REM), stage one sleep, stage two sleep, stage three sleep, and stage four sleep. At least a sensor 116 may be a part of system 100 or may be a separate device in communication with system 100.

Still referring to FIG. 1, at least a health measurement may include any result of any medical test, physiological assessment, cognitive assessment, psychological assessment, or the like. System 100 may receive at least a health measurement from one or more other devices after performance; system 100 may alternatively or additionally perform one or more assessments and/or tests to obtain at least a health measurement, and/or one or more portions thereof, on system 100. For instance, at least health measurement may include or more entries by a user in a form or similar object; one or more entries may include, without limitation, user responses to questions on a psychological, behavioral, personality, or cognitive test. For instance, a processor may present to user a set of assessment questions designed or intended to evaluate a current state of mind of the user, a current psychological state of the user, a personality trait of the user, or the like; a processor may provide user-entered responses to such questions directly as at least a health measurement and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a health measurement may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

With continued reference to FIG. 1, at least a health measurement may be obtained periodically from a user client device and stored within user database. "Periodically" as used in this disclosure, includes receiving at least a health measurement at intervals where intervals indicate a particular passage of time. For instance and without limitation, at least a health measurement may be obtained periodically every two years, every two months, every two weeks, every two minutes, every two seconds, every two meals, and the like. Intervals at which a particular health measurement is received may be determined by an informed advisor. An informed advisor, as used in this disclosure, includes a person who is licensed by a state, federal, and/or international licensing agency that helps in identifying, preventing, and/or treating illness and/or disability. An informed advisor may include persons such as a functional medicine doctor, a doctor of osteopathy, a nurse practitioner, a physician assistant, a Doctor of Optometry, a doctor of dental medicine, a doctor of dental surgery, a naturopathic doctor, a doctor of physical therapy, a nurse, a doctor of chiropractic medicine, a doctor of oriental medicine and the like. An informed advisor may include other skilled professionals such as nurses, respiratory therapists, pharmacists, home health aides, audiologists, clinical nurse specialists, nutritionists, dieticians, clinical psychologists, psychiatric mental health nurse practitioners, spiritual coaches, life coaches, holistic medicine specialists, acupuncturists, reiki masters, yoga instructors, holistic health coaches, wellness advisors and the like. For instance and without limitation, an informed advisor may direct a user who has been diagnosed with type two diabetes mellitus to obtain a health measurement such as a blood glucose reading two hours after each meal that the user consumes. In yet another non-limiting example, an informed advisor may direct a user who has been diagnosed with epilepsy to obtain a health measurement such as an electroencephalogram every six months. In yet another non-limiting example, an informed advisor may direct a user who has no diagnosed medical conditions to obtain a chem-7 basic panel once per year. Intervals at which a particular health measurement is received may be determined by a user who may seek to collect health measurements on himself or herself at varied times. For instance and without limitation, a user may have a natural curiosity and may seek to record measurements such as user's sleeping habits every night. In yet another non-limiting example, a user may be recovering from a particular illness or medical condition and may seek to track a particular health measurement over time such as user's food intolerances or markers of gut health and inflammation.

With continued reference to FIG. 1, label generator module 108 receives a periodic longevity factor 112 from a user client device 120. User client device 120 may include without limitation, a display in communication with a processor where a display may include any display as described herein. User client device 120 may include an additional computing device, such as a mobile device, laptop, desktop computer, and the like.

With continued reference to FIG. 1, label generator module retrieves a user periodic longevity factor training set 124 from a user database as described in more detail below.

With continued reference to FIG. 1, one or more periodic longevity factor 112 received from a user client device 120 may be stored in a user database 128. User database 128 may be implemented, without limitation, as a relational database, a key-value retrieval datastore such as a NOSQL database, or any other format or structure for use as a datastore that a person skilled in the art would recognize as suitable upon review of the entirety of this disclosure. One or more periodic longevity factor 112 may be stored within user database 128 in any suitable data and/or data type. For instance and without limitation, one or more periodic longevity factor 112 may include textual data such as numerical, character, and/or string data. Textual data may include a standardized name and/or code for a disease, disorder, measurement, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as periodic longevity factor 112 may take; persons skilled in the art, upon reviewing the entirety of this disclosure, will be aware of various forms which may be suitable for use as periodic longevity consistently with this disclosure.

With continued reference to FIG. 1, user database 128 may store one or more periodic longevity factor 112 as image data, such as for example, a computed tomography (CT) scan or a magnetic resonance image (MRI). Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, a "user identifier" as used in this disclosure, includes any data that uniquely identifies a particular user. Data may include a user's name, a user's date of birth, a user's medical identification number, a public and/or private key pair, a cryptographic hash, a biometric identifier such as an iris scan, fingerprint scan, a palm vein scan, a retina scan, facial recognition, DNA, a personal identification number, a driver's license or passport, token-based identification systems, digital signatures, and the like. A user identifier may be an identifier that is unique as compared to any other user identifier within system 100. A user identifier may include a statistically ensured unique identifier such as a global unique identifier (GUID) or a universally unique identifier (UUID).

With continued reference to FIG. 1, user periodic longevity factor 112 may be received by a processor 104 from an advisor client device 132. An "advisor client device 132" as used in this disclosure, includes any device suitable for use as user client device 120 as described above. An advisor client device 132 may be operated by an informed advisor, including any of the informed advisors as described above. In an embodiment, an informed advisor may transmit a user periodic longevity factor 112 to a processor 104 such as when a user periodic longevity factor 112 may be measured by or under the supervision of an informed advisor, such as for example a breast biopsy or a cerebrospinal fluid analysis.

With continued reference to FIG. 1, label generator module 108 is configured to retrieve training data in the form of a user periodic longevity factor training set 124 from a user database 128. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a server may correlate any input data as described in this disclosure to any output data as described in this disclosure.

With continued reference to FIG. 1, system 100 may include a language processing module 136. Language processing module 136 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 136 may compare extracted words to categories of advisory inputs, such data for comparison may be entered on processor 104 as described above using expert data inputs or the like. In an embodiment, one or more categories may be enumerated, to find total count of mentions in such documents. Alternatively or additionally, language processing module 136 may operate to produce a language processing model. Language processing model may include a program automatically generated by processor 104 and/or language processing module 136 to produce associations between one or more words extracted from at least a document and detect associations, including without limitation mathematical associations, between such words, and/or associations of extracted words with categories of dietary data, relationships of such categories to alimentary labels, and/or categories of alimentary labels. Associations between language elements, where language elements include for purposes herein extracted words, categories of advisory interactions, relationships of such categories to users, and/or categories of expert inputs may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of advisory interaction summary, a given relationship of such categories to users, and/or a given category of expert inputs. As a further example, statistical correlations and/or mathematical associations may include probabilistic formulas or relationships indicating a positive and/or negative association between at least an extracted word and/or a given category of advisory interaction summaries, a given relationship of such categories to users, and/or a given category of expert inputs; positive or negative indication may include an indication that a given document is or is not indicating a category of an advisory interaction summary, relationship of such category to a user, and/or category of expert inputs is or is not significant. For instance, and without limitation, a negative indication may be determined from a phrase such as "joint pain was not found to be associated with hypothyroidism" whereas a positive indication may be determined from a phrase such as "joint pain was found to be associated with osteoarthritis" as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at processor 104, or the like.

Still referring to FIG. 1, language processing module 136 and/or processor 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word and a category of an advisory interaction summary, a given relationship of such categories to users, and/or a given category of expert inputs. There may be a finite number of category of dietary data, a given relationship of such categories to advisory interaction summaries, and/or a given category of expert input to which an extracted word may pertain; an HMM inference algorithm, such as the forward-backward algorithm or the Viterbi algorithm, may be used to estimate the most likely discrete state given a word or sequence of words. Language processing module 136 may combine two or more approaches. For instance, and without limitation, machine-learning program may use a combination of Naïve-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 136 may use a corpus of documents to generate associations between language elements in a language processing module 136, and processor 104 may then use such associations to analyze words extracted from one or more documents and determine that the one or more documents indicate significance of a category of advisory interaction summary, a given relationship of such categories to users, and/or a given category of expert inputs. In an embodiment, processor 104 may perform this analysis using a selected set of significant documents, such as documents identified by one or more experts as representing good science, good clinical analysis, or the like; experts may identify or enter such documents via graphical user interface 164 as described below in more detail or may communicate identities of significant documents according to any other suitable method of electronic communication, or by providing such identity to other persons who may enter such identifications into processor 104. Documents may be entered into processor 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, processor 104 may automatically obtain the document using such an identifier, for instance by submitting a request to a database or compendium of documents such as JSTOR as provided by Ithaka Harbors, Inc. of New York.

With continued reference to FIG. 1, "user periodic longevity factor training set 124" as used in this disclosure, contains a plurality of user data entries containing user periodic longevity factors containing co-occurring periodic longevity classification labels 148. User periodic longevity factor training set 124 is composed of data entries containing a user's own data entries. For instance and without limitation, previously received periodic longevity factor 112 may be stored within user database 128 and retrieve as user periodic longevity factor training set 124. A user's own previously collected and/or recorded periodic longevity factor 112 may be utilized as a user's own training set to generate classification algorithms as described in more detail below. User periodic longevity factor training set 124 may be stored within user database 128. User database 128 may include any data structure as described above. A plurality of user periodic longevity data may be obtained from previously received from user periodic longevity factor 112 inputs may be stored within user database 128 as described above in more details. User periodic longevity data previously received may have been previously processed and classified by a processor to contain periodic longevity classification label 148. A "periodic longevity classification label 148" as used in this disclosure, includes an indicator that a particular user periodic longevity factor 112 belongs to a specific class or not based on a common property and/or attribute. Periodic longevity classification label 148 may be generated by classification algorithms that may generate classification models that draw a conclusion from input values given for training data. Classification algorithms may predict periodic longevity classification label 148 for new data. A processor 104 and/or label generator module 108 may be configured to calculate classification algorithms including for example, linear classifiers such as logistic regression, Naïve Bayes classifiers, fisher's linear discriminant, least squares support vector machines, quadratic classifiers, k-nearest neighbor classifiers, random forests, kernel estimation, decision trees, random forests, neural networks, learning vector quantization and the like. A processor 104 and/or label generator module 108 may classify user periodic longevity factors to co-occurring periodic longevity classification labels to achieve desired inputs and outputs.

With continued reference to FIG. 1, periodic longevity classification label 148 may indicate whether a particular periodic longevity factor 112 contains health data that is within normal limits and/or contains expected results and normal findings or whether a particular periodic longevity factor 112 contains health data that is not within normal limits and/or does not contain expected results and abnormal findings. Normal limits may include reference ranges deemed acceptable such as those endorsed by specific medical agencies, medical agencies, laboratories, health care systems, and the like. For instance and without limitation, normal limits may be set by the AMERICAN MEDICAL ASSOCIATION of Chicago, Illinois or the INSTITUTE FOR FUNCTIONAL MEDICINE of Federal Way, Washington, or the AMERICAN ACADEMY OF ANTI-AGING MEDICINE (A4M) of Boca Raton, Fl. and the like. In an embodiment, particular numbers of periodic longevity classification label 148 that may be generated by a processor 104 and/or label generator module 108 may be selected based on expert input. Expert input may include input received from top functional medicine doctors practicing in particular fields or specialties, journal submissions, articles and the like. Expert input may be stored within an expert database 140. Expert database 140 may include any data structure suitable for use as user database 128 as described above. Expert database 140 may include one or more expert inputs relating to periodic longevity classification label 148, clustering algorithms, and the like. Expert inputs may be received from a transmission from an advisor client device 132 as described above in more detail.

With continued reference to FIG. 1, label generator module 108 retrieves user periodic longevity factor training set 124 from user database 128 utilizing the user identifier. In an embodiment, label generator module 108 may compare a user identifier received with a periodic longevity factor 112 to a user identifier contained within the user database 128. Comparing may include determining if the user identifier received with a periodic longevity factor 112 is identical to a user identifier contained within the user database 128. For instance and without limitation, label generator module 108 may determine that a user's name and date of birth matches with a user's name and date of birth stored within the user database 128.

With continued reference to FIG. 1, label generator module 108 may retrieve a particular set of user periodic longevity factor training set 124 where the training data may include a plurality of user data entries selected as a function of an advisory input. Label generator module 108 is configured to receive a periodic longevity selector input from an advisor client device 132. A "periodic longevity selector input" as used in this disclosure, includes any input received from a device operated by an informed advisor that indicates a particular preference to select specific user data entries to be included in user periodic longevity factor training set 124. A device operating by an informed advisor may include any device suitable for use as advisor client device as described herein. A particular preference includes an indication to select user data entries that were collected during a specific period of time, user data entries that contain a particular health measurement, user data entries that were collected at a specific location, user data entries that were within reference range, user data entries that were not within reference range, user data entries that contain particular classification labels, and the like. Label generator module 108 filters the plurality of user periodic longevity data as a function of a periodic longevity selector input. For instance and without limitation, a periodic longevity selector input may indicate an informed advisor's preference to select user data entries collected between March and June of a specific year during which time user was critically ill. Label generator module 108 may filter the plurality of user periodic longevity data stored within user database 128 to select data entries containing periodic longevity data containing periodic longevity classification label 148 from March through June. In yet another non-limiting example, a periodic longevity selector input may indicate an informed advisor's preference to select user data entries that were collected while a user was on a beach vacation in Hawaii for three months. In such an instance, label generator module 108 may filter the plurality of user periodic longevity data stored within user database 128 to select data entries containing periodic longevity data containing periodic longevity classification label 148 collected during the three-month period user was in Hawaii. In an embodiment, an informed advisor who does not generate a periodic longevity selector input or who does not have a particular preference as to particular user data entries containing periodic longevity data may cause label generator module 108 to select all user data entries containing periodic longevity data containing periodic longevity classification label 148 that may be stored in user database 128 that may be utilized as user periodic longevity factor training set 124.

With continued reference to FIG. 1, label generator module 108 generates a naïve Bayes classification algorithm 144. Naïve Bayes classification algorithm 144 generates classifiers assigning class labels to problem instances, represented as vectors of feature values. Classifiers utilize periodic longevity factors as inputs and output periodic longevity classification labels. Class labels are drawn from a finite set. Naïve Bayes classification algorithm may include generating a family of algorithms that assume that the value of a particular feature is independent of the value of any other feature, given a class variable. Naïve Bayes classification algorithm may be based on Bayes Theorem expressed as $P(A/B)=P(B/A)\ P(A)\div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming classification training data 128 into a frequency table. Label generator module 108 may then calculate a likelihood table by calculating probabilities of different data entries and classification labels. Label generator module 108 utilizes a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm 144 may include a multinomial model that is used for discrete counts. Naïve Bayes classification algorithm 144 may include a Bernoulli model that may be utilized when feature vectors are binary. Naïve Bayes classification algorithm utilizes a series of one or more equations, calculations, sequence of instructions, data processing, automated reasoning and the like to utilize a periodic longevity factor 112 as input and output a periodic longevity classification label 148. For instance and without limitation, Naïve Bayes classification algorithm 144 may utilize a user periodic longevity factor 112 containing a user's hemoglobin A1c level of 7.4% as input, calculate a series of one or more equations and calculations to generate a periodic longevity classification label 148 that contains a periodic longevity classification label 148 that contains a "not normal" periodic longevity classification label 148 that indicates that the user periodic longevity factor 112 is not within normal limits.

With continued reference to FIG. 1, system 100 includes a clustering module 152. Clustering module 152 may be implemented as any hardware and/or software module. Clustering module 152 is designed and configured to receive a user adherence factor 156 containing the user identifier from the user client device 120; retrieve a user adherence factor training set from the user database 128 as a function of the user identifier wherein the user adherence factor training set contains a plurality of unclassified user data entries containing user adherence data; and generate a k-means clustering algorithm using the user adherence factor training set wherein the k-means clustering algorithm utilizes the user adherence factor 156 as an input and outputs a definite number of classified dataset clusters each containing cluster adherence label 172 wherein the user adherence factor 156 is assigned to a particular classified dataset cluster containing a cluster adherence label 172 as a function of generating the k-means clustering algorithm.

With continued reference to FIG. 1, a "user adherence factor" as used in this disclosure includes any element of data describing a user's commitment, progress, action, effort, and/or any lack thereof towards implementing and/or completing an ameliorative plan. A user adherence factor may include one or more categories of effort, progress, and/or any lack thereof that a user may attempt to achieve. For example, a user adherence factor may be rated on a continuum that may include one or more categories such as initiating when a user first begins an ameliorative plan, partly completed when a user has commenced and is underway with achieving an ameliorative plan, continuing when a user is continuing to implement or practice a particular ameliorative plan, complete when a user has completed a particular ameliorative plan, on hold when a user has put practicing a particular ameliorative plan on hold, and/or incomplete when a user stops practicing a particular ameliorative plan. An "ameliorative plan" as used in this disclosure, includes identification of one or more ameliorative processes which includes any process that improves a physical condition of a user, where a physical condition of a user may include, without limitation, any physical condition identifiable using a diagnosis by an informed advisor. A "diagnosis" as used in this disclosure, includes the determination of the nature of a cause of a disease. A diagnosis may include a description of the cause, nature, manifestation, situation, problem, and the like. A diagnosis may be generated by an informed advisor based on findings from a physical examination of a user, an interview with a user and a user's family, medical history of the user and user's family, and/or clinical findings as reported by laboratory tests, radiologic studies, medical tests, medical imaging, and the like. An ameliorative plan may include one or more ameliorative processes which may include, without limitation, exercise programs including, amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more relaxation therapies including meditation, massage, Reiki, acupuncture, craniosacral massage, chiropractic adjustments, and the like. Ameliorative processes may include one or more medications, supplements, nutraceuticals, herbals, vitamins, minerals, homeopathic remedies, nutritional supplements and the like. Persons skilled in the art, upon reviewing the entirety of this disclosure, will be aware of various processes that may be used as ameliorative processes consistently with this disclosure. Ameliorative plan may be generated and created by one or more informed advisors who may be coordinating the care and/or actively treating a user. One or more ameliorative plans pertaining to a user may be stored in user database 128.

With continued reference to FIG. 1, clustering module 152 receives a user adherence factor 156 containing a user identifier. User identifier includes any of the user identifiers as described above. Clustering module 152 retrieves a user adherence factor training set 160 from a user database 128 utilizing the user identifier. A "user adherence factor training set 160" as used in this disclosure, includes a plurality of unclassified data entries containing user adherence data. "Unclassified data entries" as used in this disclosure, includes one or more data entries that have not been utilized in combination with one or more classification algorithms to generate one or more classification labels. Classification algorithms include any of the classification algorithms as described above including logistic regression, Naïve Bayes, decision trees, k-nearest neighbors, and the like. A "classification label" as used in this disclosure, includes any identification as to whether a particular data entries or series of data entries belong to a class or not. Classification may include the process of assigning a set of predefined categories or classes to one or more data entries utilizing classification algorithms. Predefined categories or classes may be generated and/or selected based on expert input, such as from expert database 140 as described above. For instance and without limitation, predefined categories or classes may be selected from expert database 140 that classify data entries based on whether a particular user adherence factor 156 indicates if a user has been adherent with an ameliorative plan or not. For instance and without limitation, an ameliorative plan may include an ameliorative process that specifies user should initiate a yoga practice three times per week. In such an instance, clustering module 152 may receive a user adherence factor 156 that contains a description of four yoga classes user attended in the previous week, which may be stored within user database 128 as an unclassified user data entry. Clustering module 152 may select such an entry to be utilized as user adherence factor training set 160.

With continued reference to FIG. 1, a user adherence factor 156 may be generated by an informed advisor. An informed advisor, including any of the informed advisors as described above, may generate a user adherence factor 156 on a graphical user interface 164 located on a processor. Graphical user interface 164 may include without limitation, a form or other graphical element having data entry fields, where a comprehensive advisor may enter a user adherence factor 156. Graphical user interface 164 may include data entry fields that allow for an informed advisor to enter free form textual inputs. Graphical user interface 164 may provide drop-down lists, where users such as an informed advisor may select one or more entries pertaining to a user. Graphical user interface 164 may include touch options where a user may enter a command by touching and selecting a particular option. Graphical user interface 164 may include text to speech software whereby an informed advisor may speak a particular command including a user adherence factor 156 and graphical user interface 164 may convert the spoken command into a textual output that is displayed on a graphical user interface 164. For instance and without limitation, an informed advisor such as a user's functional medicine physician may generate a user adherence factor 156 on a graphical user interface 164 located on a processor after meeting with user for an appointment and discussing user's adherence in regard to a particular ameliorative plan. In yet another non-limiting example, an informed advisor such a user's meditation instructor may enter a user adherence factor 156 on a graphical user interface 164 located on a processor after user failed to show up for a series of scheduled meditation sessions with user's meditation instructor. In an embodiment, user adherence factor 156 containing a user identifier may be generated by an informed advisor on an advisor client device 132 and transmitted to a processor 104 utilizing any network topography as described herein.

With continued reference to FIG. 1, clustering model may retrieve a user adherence factor training set 160 from a user database 128 based on advisory input. Clustering module 152 is configured to receive an adherence factor selector input from an advisor client device 132. An "adherence factor selector input" as used in this disclosure, includes any input received from an advisor client device operated by an informed advisor that indicates a particular preference to select specific adherence factors stored within user database 128 to be utilized in a user adherence factor training set. A particular preference includes an indication to select user adherence factor 156 generated only by a user, to select user adherence factor 156 generated only by one or more informed advisors, to select user adherence factor 156 generated in regard to a particular ameliorative plan, to select user adherence factor 156 generated in regards to particular levels of adherence and the like. For instance and without limitation, an informed advisor may generate an adherence factor selector input that indicates a preference for an informed advisor to utilize unclassified user data entries containing user adherence data over a particular period of time when a user was started on a new ameliorative plan by the particular informed advisor entering the adherence factor selector input. Clustering module 152 filters a plurality of unclassified data entries containing user adherence data as a function of an adherence factor selector input. Filtering may include selecting particular unclassified user data entries containing user adherence data to be utilized as a user adherence factor training set 160 such as selecting unclassified data entries collected during a particular period of time or selecting unclassified data entries that relate to a particular ameliorative plan. Filtering may include discarding particular unclassified user data entries containing user adherence data as a function of an adherence factor selector input such as discarding unclassified user data entries that were not collected during a particular time period or that were collected in reference to a separate ameliorative plan which may be outdated or user may have been unable to complete. In an embodiment, an informed advisor who does not generate an adherence factor selector input or who does not have a particular preference as to particular unclassified user data entries may cause clustering module 152 to select all unclassified user data entries containing user adherence data that may be stored in user database 128 as user adherence factor 156 training data.

With continued reference to FIG. 1, clustering module 152 is configured to generate a k-means clustering algorithm 168. A "k-means clustering algorithm" as used in this disclosure, includes cluster analysis that partitions n observations or unclassified cluster data entries into k clusters in which each observation or unclassified cluster data entry belongs to the cluster with the nearest mean. Cluster data entry may include data entries selected from a clustering dataset. Cluster data entry may be received from clustering database. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, clustering module 152 generates a k-means clustering algorithm containing unclassified data as input and outputs a definite number of classified data entry cluster wherein the data entry clusters each contain cluster data entries. Clustering module 152 may select a specific number of groups or clusters to output, identified by the variable "k." Generating a k-means clustering algorithm includes assigning inputs containing unclassified data to a "k-group" or "k-cluster" based on feature similarity. Centroids of k-groups or k-clusters may be utilized to generate classified data entry cluster. Clustering module 152 by select "k" variable by calculating k-means clustering algorithm for a range of k values and comparing results. Clustering module 152 may compared results across different values of k as the mean distance between cluster data entries and cluster centroid. Clustering module 152 may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. Clustering module 152 may select a k value by classifying a user adherence factor 156. Clustering module 152 may evaluate a user adherence factor 156 to determine a cluster adherence label 172. A "cluster adherence label 172" as used in this disclosure, includes a label categorizing a particular user adherence factor 156 as belonging to a particular group or cluster based on a shared commonality. Clustering module 152 utilizes a cluster adherence label 172 to select a definite number of classified data entry cluster or k-value. In an embodiment, a particular cluster adherence label 172 may indicate a preferred k-value based on previous data collections and calculations. For instance and without limitation, a cluster adherence label 172 that indicates adherence may be best suited for a k-value of 17 while a cluster adherence label 172 that indicates nonadherence may be best suited for a k-value of 144. In an embodiment, a k-value may be selected based on input from expert database 140 as described above in more detail.

With continued reference to FIG. 1, generating a k-means clustering algorithm includes generating initial estimates for k centroids which may be randomly generated or randomly selected from unclassified data input. K centroids may be utilized to define one or more clusters. Clustering module 152 may assign unclassified data to one or more k-centroids based on the squared Euclidean distance by first performing a data assigned step of unclassified data. Clustering module 152 may assign unclassified data to its nearest centroid based on the collection of centroids ci of centroids in set C. Unclassified data may be assigned to a cluster based on $argmin_{ci \exists c}$ dist(ci, x)$^2$, where argmin includes argument of the minimum; ci includes a collection of centroids in a set C; and dist includes standard Euclidean distance. Clustering module 152 may then recompute centroids by taking mean of all cluster data entries assigned to a centroid's cluster. This may be calculated based on ci=1/|Si|Σxi∈Si$^{xi}$. Clustering module 152 may continue to repeat these calculations until a stopping criterion has been satisfied such as when cluster data entries do not change clusters, the sum of the distances have been minimized, and/or some maximum number of iterations has been reached.

With continued reference to FIG. 1, clustering module 152 uses user adherence factor 156 as an input and outputs a definite number of classified dataset clusters each containing cluster adherence label 172. A "cluster adherence label 172" as used in this disclosure, includes any unique identifier of a particular cluster. In an embodiment, a cluster adherence label 172 may uniquely identify shared characteristics or commonalities of user data entries contained with a particular cluster. In an embodiment, user data entries may be selected to be in particular clusters based on level of adherence contained within user data entries containing user adherence data. In such an instance, cluster adherence label 172 may indicate the level of adherence of each cluster. For instance and without limitation, a cluster adherence label 172 may reflect particular levels of adherence such as data entries that are adherent, data entries are moderately adherent, data entries that are mildly adherent, and data entries that are not adherent. Adherence levels may be based on a continuum or may be reflected as a particular percentage reflecting an overall adherence percentage.

With continued reference to FIG. 1, system 100 includes a processing module 176. Processing module 176 may be implemented as any hardware and/or software module. Processing module 176 is designed and configured to receive the periodic longevity factor 112 and the periodic longevity classification label 148 from the label generator module 108; receive the user adherence factor 156 assigned to the particular classified dataset clustering containing the cluster adherence label 172; retrieve a user ameliorative plan 180 from the user database 128 as a function of the user identifier wherein the user ameliorative plan 180; evaluate the user ameliorative plan 180 as a function of the periodic longevity classification label 148 and the cluster adherence label 172; generate an updated user ameliorative plan 184 as a function of evaluating the user ameliorative plan 180; and display the updated user ameliorative plan 184 on a graphical user interface 164 located on the processor.

With continued reference to FIG. 1, processing module 176 retrieves a user ameliorative plan 180 from user database 128 as a function of a user identifier. User ameliorative plan 180 may include any of the ameliorative plans as described above. Processing module 176 may select a user ameliorative plan 180 from user database 128 by matching user identifier contained within a user periodic longevity factor 112 and/or user adherence factor 156. Processing module 176 may match and confirm a user identifier contained within a user periodic longevity factor 112 and/or user adherence factor 156 to a user identifier contained within user database 128. For instance and without limitation, processing module 176 match a user's name and date of birth contained within a user periodic longevity factor 112 to a user's name and date of birth contained within a user database 128. In an embodiment, processing module 176 may retrieve a user ameliorative plan 180 based on an informed advisor identifier contained within an ameliorative plan. Informed advisor identifier may include an identifier that uniquely identifiers a particular informed advisor who initiated and/or generated a particular ameliorative plan for a user. Informed advisor identifier may include any identifier suitable for use as user identifier as described above. For instance and without limitation, informed advisor identifier may indicate that a particular cardiologist initiated an ameliorative plan for a user. Ameliorative plan includes at least an ameliorative process. At least an ameliorative process includes any of the ameliorative processes as described above. For instance and without limitation, an ameliorative plan may include an ameliorative process such as a particular exercise routine or a particular nutraceutical supplement regimen that a user should consume. Ameliorative plan may be generated by one or more informed advisors. Informed advisor may have a relationship with a user and may provide medical advice and counsel a user on particular aspects of a user's life. For instance and without limitation, an informed advisor may include a user's yoga instructor who may generate an ameliorative plan containing a particular yoga sequence that a user should practice. In yet another non-limiting example, an informed advisor may include a user's functional medicine physician who may generate an ameliorative plan containing a particular dietary regimen that a user is instructed to follow.

With continued reference to FIG. 1, processing module 176 is configured to evaluate a user ameliorative plan 180 utilizing the periodic longevity classification label 148 and the cluster adherence label 172. Evaluating may include determining whether a particular user periodic longevity factor 112 containing a periodic longevity classification label 148 reflects that a particular ameliorative plan is having a positive impact on a user's health and wellness. For instance and without limitation, an ameliorative plan may contain a particular health goal that a user needs to achieve such as a particular periodic longevity factor 112 or health measurement that an informed advisor may seek to achieve by implementing a particular ameliorative plan. For example, an ameliorative plan may contain a goal health measurement generated by an informed advisor that indicates an informed advisor's recommendation to decrease a user's hemoglobin A1C to 5.0 after initiation of an ameliorative plan that includes starting a user and maintaining the user on a paleo diet. Processing module 176 may evaluate the periodic longevity factor 112 containing a user's hemoglobin A1C to determine if a user has achieved the informed advisor's recommendation to have a hemoglobin A1C of 5.0. Processing module 176 may evaluate a periodic longevity classification label 148 to determine if it contains a normal label indicating that a particular periodic longevity factor 112 is within range or if a periodic longevity classification label 148 contains a not normal label indicating that a particular periodic longevity factor 112 is not within range. Evaluating may include determining whether a particular user adherence factor 156 containing a cluster adherence label 172 indicates that a user has been adherent or not. In an embodiment, ameliorative plan may contain a goal adherence level generated by an informed advisor that indicates an informed advisor's recommendation as to what level or spectrum of adherence an informed advisor wishes to see from a user when implementing a particular ameliorative plan. For example, a particular ameliorative plan may contain a goal adherence level that indicates an informed advisor's recommendation for a user to engage in physical activity a minimum of three days each week. Processing module 176 may evaluate a user ameliorative plan 180 by comparing a user adherence factor 156 to a goal adherence level contained within an ameliorative plan. Evaluating may include determining if a cluster adherence label 172 indicates a particular level of adherence or nonadherence.

With continued reference to FIG. 1, processing module 176 may evaluate a particular user ameliorative plan 180 based on advisory input. In an embodiment, processing module 176 may assess a periodic longevity factor 112 and a periodic longevity classification label 148 to determine if a periodic longevity classification label 148 contains an alert condition. An "alert condition" as used in this disclosure, includes any situation when a periodic longevity factor 112 contains a health measurement that is outside of normal reference range limits or contains abnormal findings. For instance and without limitation, a fasting blood sugar level of 137 mg/dL includes an alert condition as compared to a normal reference range of 0-100 mg/dL. In yet another non-limiting example, a brain scan that shows three separate brain lesions may contain an alert condition as compared to a normal brain scan that does not contain any lesions. An alert condition may prompt processing module 176 to display the periodic longevity factor 112 and a periodic longevity classification label 148 containing an alert condition on a graphical user interface 164 located on a processor. In an embodiment, this may be displayed for an informed advisor and may be transmitted to an advisor client device 132 utilizing any network methodology as described herein. Processing module 176 may receive an advisory input generated on a graphical user interface 164 located on a processor 104 as a function of the alert condition. An "advisory input" as used in this disclosure, includes any feedback or response from an informed advisor. Feedback may include a request for a consultation event, such as when an informed advisor may wish to speak with a user in regard to an alert condition or when an informed advisor may wish to see a user for a follow up appointment. Response may include an informed advisor's medical opinion that a particular alert condition may not require medical intervention and may be a normal occurrence for a particular user.

With continued reference to FIG. 1, processing module 176 may evaluate ameliorative plan to determine if an adherence cluster label contains a non-adherence label. A "non-adherence label" as used in this disclosure, includes any cluster label that indicates non-adherence by a user with a particular ameliorative plan. Non-adherence label may include one or more labels indicting particular levels and/or times of non-adherence. For example, non-adherence label may contain one or more temporal attributes detailing specific periods of non-adherence such as non-adherence within the past week, non-adherence within the past month, non-adherence within the past three days and the like. Non-adherence label may also indicate particular variants of non-adherence such as always non-adherent when a user is never adherent or never implements or practices a particular ameliorative plan, moderately non-adherent when a user does not practice or implement a particular ameliorative plan most of the time, mildly non-adherent when a user does not practice or implement a particular ameliorative plan infrequently or only one or two days each week, and/or adherent when a user routinely and regularly practices and/or implements a particular ameliorative plan almost exclusively every day. Processing module 176 may display a user adherence factor 156 and a cluster adherence label 172 containing a non-adherence label on a graphical user interface 164 located on a processor. Processing module 176 may display a user adherence factor 156 and a cluster adherence label 172 for an informed advisor. Processing module 176 may receive an advisory input generated on a graphical user interface 164 located on a processor as a function of a non-adherence label. An advisory input may include any of the advisory inputs as described above.

With continued reference to FIG. 1, processing module 176 is configured to generate an updated user ameliorative plan 184. Generating an updated user ameliorative plan 184 may include displaying a periodic longevity classification label 148 and a cluster adherence label 172 on a graphical user interface 164 located on a processor and receiving an advisory input based on displaying the periodic longevity classification label 148 and the cluster adherence label 172. Advisory input may include any of the advisory input as described above. For instance and without limitation, an advisory input may include a recommendation for a user to increase user's intake of a particular supplement from 3 capsules per day to 4 capsules per day. In such an instance, ameliorative plan may be updated to reflect an informed advisor's recommendation. Generating an updated user ameliorative plan may include transmitting to a user client device a request for one or more additional periodic longevity factors, such as when additional data may need to be analyzed. Generating an updated user ameliorative plan may include transmitting to a user client device a request for one or more additional user adherence factors such as when a processor 104 may need additional data such as from an advisory input requesting further adherence information.

With continued reference to FIG. 1, processing module 176 may generate an updated user ameliorative plan 184 by generating one or more supervised machine-learning algorithms. An "updated user ameliorative plan 184" as used in this disclosure, includes an ameliorative plan that includes one or more changes to one or more ameliorative process contained within an ameliorative plan. A change, may include any difference to a particular ameliorative process such as replacing a first ameliorative process with a second ameliorative process, increasing or decreasing the frequency of practicing a particular ameliorative process, increasing or decreasing the intensity of a particular ameliorative process, adding a second and third ameliorative process to a first ameliorative process and the like. Processing module 176 may select ameliorative training set from an ameliorative training set database 188 utilizing periodic longevity classification label 148 and a cluster adherence level to select a particular training set. Ameliorative training set may include any of the ameliorative training set as described above. Ameliorative training set may include a plurality of data entries containing a first ameliorative plan containing a periodic longevity classification label 148 and a cluster adherence label 172 correlated to a second ameliorative plan. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of a first ameliorative plan containing a periodic longevity classification label 148 and a cluster adherence label 172 as inputs, a second ameliorative plan as outputs, and a scoring function representing a desired form of relationship to be detected between elements of a first ameliorative plan containing a periodic longevity classification label 148 and a cluster adherence label 172 and a second ameliorative plan; scoring function may, for instance, seek to maximize the probability that a given element of a first ameliorative plan containing a periodic longevity classification label 148 and a cluster adherence label 172 is associated with a given priority treatment and/or a second ameliorative plan to minimize the probability that a given element of a first ameliorative plan containing a periodic longevity classification label 148 and a cluster adherence label 172 is not associated with a given second ameliorative plan. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Persons skilled in the art, upon reviewing the entirety of this disclosure, will be aware of various possible variations of supervised machine-learning algorithms that may be used to determine relation between a first ameliorative plan containing a periodic longevity classification label 148 and a cluster adherence label 172 and a second ameliorative plan. In an embodiment, one or more supervised machine-learning algorithms may be restricted to a particular domain for instance, a supervised machine-learning process may be performed with respect to a given set of parameters and/or categories of parameters that have been suspected to be related to a given set of ameliorative plans, and/or are specified as linked to a medical specialty and/or field of medicine covering a particular body system or medical specialty. As a non-limiting example, a particular periodic longevity classification label 148 may indicate an emergency medical condition and may be typically associated with a known urgency to seek medical attention and be treated, and a supervised machine-learning process may be performed to relate those first ameliorative plans to second ameliorative plans; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate priority treatments. Additional supervised learning processes may be performed without domain restrictions to detect, for instance, previously unknown and/or unsuspected relationships between first ameliorative plans and second ameliorative plans.

With continued reference to FIG. 1, processing module 176 generates using a supervised machine-learning algorithm an ameliorative model that utilizes a user ameliorative plan as an input and outputs an updated user ameliorative plan 184 utilizing ameliorative training set. Ameliorative model may include any machine-learning process that may include linear or polynomial regression algorithms, may include calculating one or more equations, may include a set of instructions to generate outputs based on inputs which may be derived using any machine-learning algorithm and the like. Ameliorative model may utilize one or more advisory inputs to output an updated user ameliorative plan. In an embodiment, an advisory input may include an input to the ameliorative model that may be utilized to generate an updated user ameliorative plan. For example, an advisory input to the ameliorative model may include selection of a particular ameliorative model or selection of a particular set of ameliorative training set. Advisory input may be received from an advisor client device operated by an informed advisor. An updated user ameliorative plan 184 may be displayed by processing module 176 on a graphical user interface 164 located on a processor.

Figure 2:
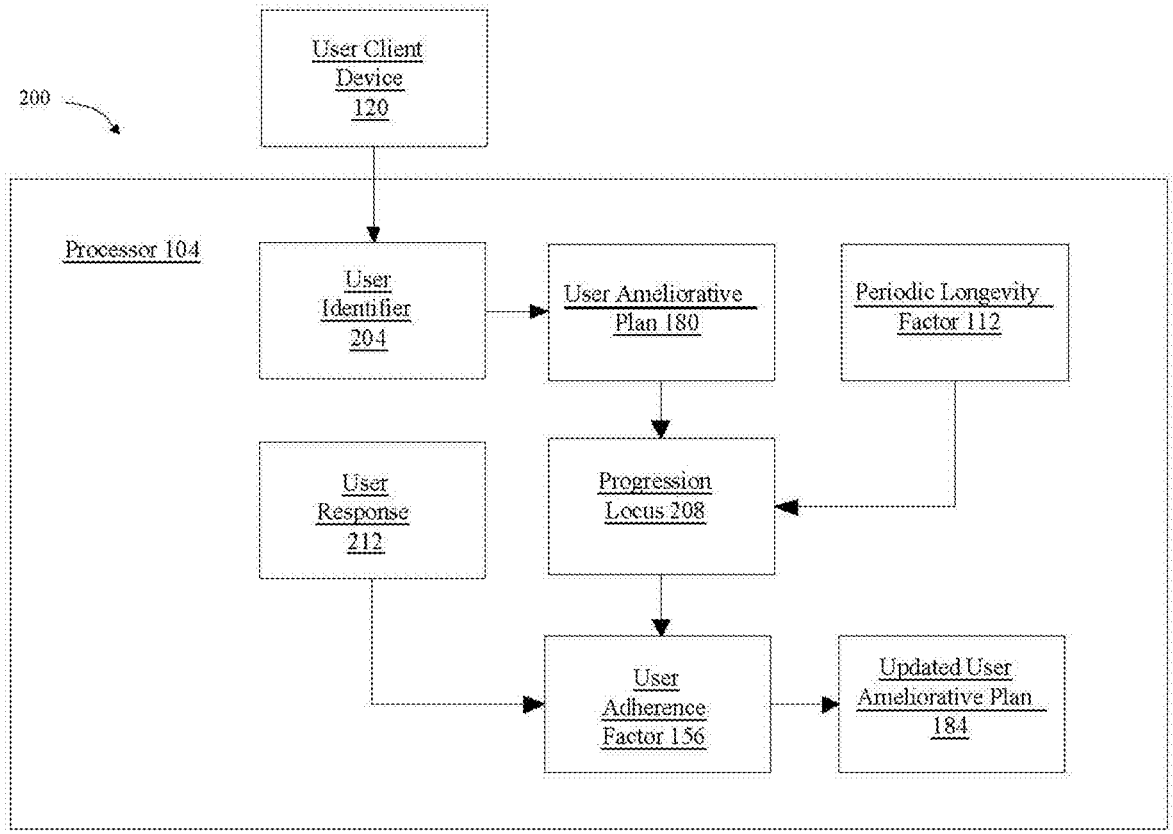
FIG. 2 is a block diagram illustrating an exemplary embodiment of a system for initiating an updated ameliorative plan.

Referring now to FIG. 2, an exemplary embodiment of a system 200 for initiating an updated user ameliorative plan is illustrated. System 200 includes a processor 104. Processor 104 may include any processor 104 as described above in reference to FIG. 1. In an embodiment, and without limitation, processor 104 may include any computing device as described herein, including without limitation a microcontroller, microprocessor, digital signal processor 104

(DSP) and/or system on a chip (SoC) as described herein. Processor 104 may be housed with, may be incorporated in, or may incorporate one or more sensor of at least a sensor. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 with one or more additional devices as described below in further detail via a network interface device. Network interface device may be utilized for connecting a processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, A processor 104 or cluster of computing devices in a first location and a second computing device or cluster of computing devices in a second location. Processor 104 may include one or more computing devices dedicated to data storage, security, distribution of traffic for load balancing, and the like. A processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of system 100 and/or computing device.

With continued reference to FIG. 2, processor 104 may be designed and/or configured to perform any method, method step, or sequence of method steps in any embodiment described in this disclosure, in any order and with any degree of repetition. For instance, a processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A processor 104 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 2, processor 104 is configured to identify a user ameliorative plan 180. User ameliorative plan 180 may include any user ameliorative plan 180 as described above in reference to FIG. 1. In an embodiment, and without limitation, user ameliorative plan 180 may include one or more programs such as a particular exercise routine or a particular nutraceutical supplement regimen that a user should consume. As a further non-limiting example, user ameliorative plan 180 may include one or more instruction sets and/or programs to affect one or more biological systems such as the integumentary system, cardiovascular system, pulmonary system, musculoskeletal system, nervous system, digestive system, and the like thereof. In an embodiment, and without limitation, user ameliorative program 180 may provide instruction relating to one or more areas of a user's life, including but not limited to, physical fitness, stress management, meditation, spirituality, religion, energy healing, professional endeavors, personal endeavors, body, mind, health, finances, recreation, romance, personal development, and the like. For example, and without limitation, user ameliorative program 180 may include a program that instructs an individual to exercise for 10 minutes each day. As a further non-limiting example, user ameliorative program 180 may include a program that instructs an individual to mediate and/or conduct a yoga exercise for 30 minutes every week. As a further non-limiting example, user ameliorative plan 180 may instruct an individual to go on a hike for 2 hours once a week. Additionally or alternatively user ameliorative plan 180 may include one or more nutrition and/or supplement plans. For example, and without limitation, nutrition and/or supplement plan may include a list of nutritional supplement and/or edibles a user should consume. As a non-limiting example, a nutrition plan may instruct an individual to consume a paleo diet. As a further non-limiting example, a supplement plan may instruct an individual to consume a 100 mg of vitamin K every other day. In an embodiment and without limitation, user ameliorative plan 180 may include one or more instructions such as, but not limited to a first instruction to exercise and a second instruction of a supplement plan.

Still referring to FIG. 2, processor 104 identifies user ameliorative plan 180 as a function of a user identifier from a client device 120. User identifier 204 includes any of the user identifier as described above, in reference to FIG. 1. For instance, and without limitation, user identifier 204 may include any data that uniquely identifies a particular user. Data may include a user's name, a user's date of birth, a user's medical identification number, a public and/or private key pair, a cryptographic hash, a biometric identifier such as an iris scan, fingerprint scan, a palm vein scan, a retina scan, facial recognition, DNA, a personal identification number, a driver's license or passport, token-based identification systems, digital signatures, and the like. User identifier 204 may be an identifier that is unique as compared to any other user identifier within system 200. User identifier 204 may include a statistically ensured unique identifier such as a global unique identifier (GUID) or a universally unique identifier (UUID). User identifier 204 is obtained from a user client device 120. User client device 120 includes any of the user client device 120 as described above, in reference to FIG. 1. For example, and without limitation, user client device 120 may include a display in communication with a processor where a display may include any display as described herein. User client device 120 may include an additional computing device, such as a mobile device, laptop, desktop computer, and the like.

Still referring to FIG. 2, processor 104 is configured to obtain a periodic longevity factor 112. Periodic longevity factor 112 may include any periodic longevity factor 112 as described above, in reference to FIG. 1. In an embodiment, periodic longevity factor 112 may include any health measurement of a user's body. In an embodiment, and without limitation, a health measurement may include a physically extracted sample, wherein a physically extracted sample is described above, in reference to FIG. 1. In another embodiment, and without limitation, a health measurement may include one or more medical tests, physiological assessments, cognitive assessments, psychological assessments, and/or the like thereof. In another embodiment, and without limitation, health measurement may include one or more entries by a user in a form or similar object; one or more entries may include, without limitation, user responses to questions on a psychological, behavioral, personality, or cognitive test. In another embodiment, and without limitation, obtaining the periodic longevity factor 112 may further comprise receiving at least a health measurement as a function of a sensor, wherein a sensor is described above in reference to FIG. 1. For example, and without limitation, sensor may include one or more medical sensors, capture sensors, electromagnetic sensors, temperature sensors, motion sensors, mobile device sensors, sleep cycle sensors, and the like thereof. Additionally or alternatively, obtaining periodic longevity factor 112 may further comprise receiving an informed advisor input. As used in this disclosure an "informed advisor input" an input and/or response from an informed advisor associated to a user's health measurement. For example, and without limitation, informed advisor input may include a physician and/or nutritionist inputting one or more assessments, questionnaires, test results, and the like thereof associated to a user.

Still referring to FIG. 2, processor 104 is configured to determine a user adherence factor 156. User adherence factor 156 may include any user adherence factor 156 as described above, in reference to FIG. 1. For example, and without limitation user adherence factor 156 may include any element of data describing a user's commitment, progress, action, effort, and/or any lack thereof towards implementing and/or completing an ameliorative plan. In an embodiment, and without limitation, user adherence factor 156 may include one or more categories of effort, progress, and/or any lack thereof that a user may attempt to achieve. In an embodiment, and without limitation, user adherence factor 156 may be represented as one or more quantitative values representing a likelihood of adherence. In an embodiment, and without limitation, determining user adherence factor 156 may further comprise identifying a compliance element. As used in this disclosure a "compliance element" is an element of data representing one or more user abilities to act according to user ameliorative plan 180. For example, and without limitation, compliance element may denote that a user is likely to comply with user ameliorative plan 156. As a further non-limiting example, compliance element may denote that a user is unlikely to comply with user ameliorative plan 156. Processor 104 determines user adherence factor 156 as a function of identifying a progression locus 208 as a function of user ameliorative plan 180 and periodic longevity factor 112. As used in this disclosure a "progression locus" is a location along a user ameliorative plan, wherein the location may represent a progress value towards completing the user ameliorative plan. a user ameliorative plan. For example, progression locus 208 may denote that user ameliorative plan 180 is 50% progressed and/or completed as a function of periodic longevity factor 112 comprising a biomarker of glucose, wherein the concentration of glucose is 100 mg/dL. As a further non-limiting example, progression locus 208 may denote that user ameliorative plan 180 is 23% progressed and/or completed as a function of periodic longevity factor 112 comprising a biomarker of C-reactive protein, wherein the concentration of glucose is 122 mg/L. In an embodiment, and without limitation, identifying progression locus 208 may further comprise determining a buffer zone as a function of user ameliorative plan 180. As used in this disclosure a "buffer zone" is a range of progression and/or success that an ameliorative plan may progress without adhering to the user ameliorative plan. For example, and without limitation, buffer zone may denote that a user ameliorative plan may be 22% progressed, wherein no adherence to the ameliorative plan is necessary. As a further non-limiting example, buffer zone may denote that a user ameliorative plan may regress as a function of no adherence to the ameliorative plan.

Still referring to FIG. 2, processor 104 receives a user response 212. As used in this disclosure a "user response" is an input and/or entry of a user associated to a user's behavior and/or opinion of user ameliorative plan. For example, and without limitation, user response 212 may include one or more entries associated to a user's enthusiasm of an ameliorative plan. As a further non-limiting example, user response 212 may include one or more entries associated to a user's despise of an ameliorative plan. In an embodiment, and without limitation, receiving user response 212 may further comprise identifying a routine element. As used in this disclosure a "routine element" is an element of data representing an individual's habits and/or tendencies. For example, and without limitation, routine element may denote that a user habitually smokes cigarettes. As a further non-limiting example, routine element may denote that a user engages in a routine of a sedentary lifestyle. In an embodiment, and without limitation, routine element may include one or more user behaviors and/or activities such as a behavior of walking, hiking, golfing, sitting, playing video games, and the like thereof. Processor 104 is configured to determine user adherence factor 156 as a function of progression locus 208 and user response 212. In an embodiment, and without limitation, processor 104 may determine user adherence factor 156 as a function of an adherence machine-learning model. As used in this disclosure "adherence machine-learning model" is a machine-learning model to produce a user adherence factor output given progression loci and/or user responses as inputs; this is in contrast to a non-machine learning software program where the commands to be executed are determined in advance by a user and written in a programming language. Adherence machine-learning model may include one or more adherence machine-learning processes such as supervised, unsupervised, or reinforcement machine-learning processes that processor 104 and/or a remote device may or may not use in the determination of user adherence factor 156. As used in this disclosure "remote device" is an external device to processor 104. Adherence machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, processor 104 may train adherence machine-learning process as a function of an adherence training set. As used in this disclosure an "adherence training set" is a training set that correlates a progression locus and/or user response to a user adherence factor. For example, and without limitation, a progression locus of 50% completion and a user response of a negative behavior and/or attitude towards the ameliorative plan may relate to a user adherence factor of low likelihood to continue and/or administer the ameliorative plan. The adherence training set may be received as a function of user-entered valuations of progression loci, user responses, and/or user adherence factors. Processor 104 may receive adherence training set by receiving correlations of progression loci, and/or user responses that were previously received and/or determined during a previous iteration of determining user adherence factors. The adherence training set may be received by one or more remote devices that at least correlate a progression locus and/or user response to a user adherence factor. The adherence training set may be received in the form of one or more user-entered correlations of a progression locus and/or user response to a user adherence factor.

Still referring to FIG. 2, processor 204 may receive adherence machine-learning model from a remote device that utilizes one or more adherence machine learning processes, wherein a remote device is described above in detail. For example, and without limitation, a remote device may include a computing device, external device, processor, and the like thereof. Remote device may perform the adherence machine-learning process using the adherence training set to generate user adherence factor 156 and transmit the output to processor 104. Remote device may transmit a signal, bit, datum, or parameter to processor 104 that at least relates to user adherence factor 156. Additionally or alternatively, the remote device may provide an updated machine-learning model. For example, and without limitation, an updated machine-learning model may be comprised of a firmware update, a software update, a adherence machine-learning process correction, and the like thereof. As a non-limiting example a software update may incorporate a new progression locus that relates to a modified user response. Additionally or alternatively, the updated machine learning model may be transmitted to the remote device, wherein the remote device may replace the adherence machine-learning model with the updated machine-learning model and determine the user adherence factor as a function of the progression locus using the updated machine-learning model. The updated machine-learning model may be transmitted by the remote device and received by processor 104 as a software update, firmware update, or corrected adherence machine-learning model. For example, and without limitation adherence machine-learning model may utilize a random forest machine-learning process, wherein the updated machine-learning model may incorporate a gradient boosting machine-learning process.

Still referring to FIG. 2, processor 104 may determine user adherence factor 156 as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Processor 104 and/or another device may generate a classifier using a classification algorithm, defined as a processes whereby a processor 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)\ P(A){\div}P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 2, processor 104 is configured to generate an updated user ameliorative plan 184 as a function of user adherence factor 156. Updated user ameliorative plan 184 may include any updated user ameliorative plan 184 as described above in reference to FIG. 1. In an embodiment, and without limitation, updated user ameliorative plan 184 may include one or more modified and/or adjusted ameliorative plans to increase and/or enhance user adherence factor 156. In an embodiment, and without limitation, generating updated user ameliorative plan 184 may further comprise identifying an optimized user adherence factor. As used in this disclosure an "optimized user adherence factor" is an enhanced and/or increased user adherence factor such that a larger likelihood for a user to adhere to ameliorative plan exists. In an embodiment, and without limitation, processor 104 may optimize user adherence factor 156 as a function of a data-flow analysis, dependence analysis, alias analysis, pointer analysis, escape analysis, and the like thereof. In an embodiment, and without limitation, processor 104 may optimize user adherence factor 156 as a function of one or more inline expansions, dead code eliminations, constant propagation, loop transformations, and/or automatic parallelization functions. In another embodiment, processor 104 may optimize user adherence factor 156 as a function of a machine dependent optimization such as a peephole optimization, wherein a peephole optimization may rewrite short sequences of code into more efficient sequences of code. In an embodiment, and without limitation, identifying optimized user adherence factor may further comprise determining a modification element. As used in this disclosure a "modification element" is an element of data representing one or more alterations of a user's behavior and/or routine that may occur to increase an adherence. For example, and without limitation, modification element may include an element of data denoting a modification to a user's nutrition may increase adherence to the ameliorative plan.

Still referring to FIG. 2, processor 104 is configured to initiate updated user ameliorative plan 184. Initiating may include any process and/or process step for initiating as described above in reference to FIG. 1. In an embodiment, and without limitation, initiating user ameliorative plan may include using an automated manufacturing system, to produce one or more edibles and/or supplements that are associated with updated user ameliorative plan 184. In another embodiment, and without limitation, initiating may include transmitting updated user ameliorative plan 184 to user client device 120. For example, and without limitation, user ameliorative plan 184 may be transmitted in the form of a signal. As used in this disclosure a "signal" is a notification and/or indicator that a user ameliorative plan should be modified to the updated user ameliorative plan. A signal may consist of a wired and/or wireless communication. The wireless communication signals may include, without limitation, radio waves, electric fields, mobile broadband, Wi-Fi, and/or the BLUETOOTH protocol promulgated by Bluetooth SIG, Inc. of Kirkland, Washington, wherein Bluetooth is a wireless technology used for exchanging data between fixed mobile devices over short distances using ultra high frequency radio waves between 2.402 GHz to 2.480 GHz. As a non-limiting example processor 104 may initiate updated user ameliorative plan via Bluetooth, with a user client device, that at least modifies and/or alters a previous user ameliorative plan.

Figure 3:
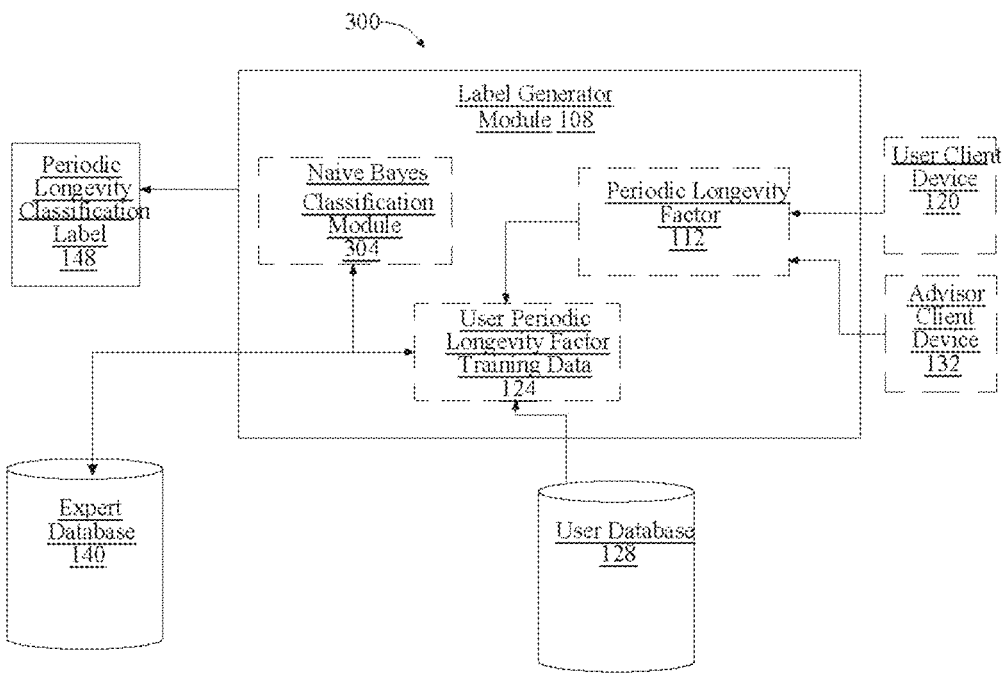
FIG. 3 is a block diagram illustrating an exemplary embodiment of a label generator module.

Referring now to FIG. 3, an exemplary embodiment 300 of label generator module 108 is illustrated. Label generator module 108 may be implemented as any hardware and/or software module. Label generator module 108 is configured to receive a periodic longevity factor 112 containing a user identifier from a user client device 120. Periodic longevity factor 112 includes any of the periodic longevity factor 112 as described above. For example, a periodic longevity factor 112 may include a blood result showing a user's intracellular calcium level. In yet another non-limiting example, a periodic longevity factor 112 may include an x-ray containing an image of a user's ankle joint. In an embodiment, label generator module 108 may receive a periodic longevity factor 112 from an advisor client device 132. In yet another non-limiting example, label generator module 108 may receive a periodic longevity factor 112 from user database 128. In an embodiment, periodic longevity factor 112 may be received by label generator module 108 periodically. Periodically includes any of the intervals as described above. For instance and without limitation, label generator module 108 may receive a periodic longevity factor 112 from a user client device 120 once every hour, once every three months, once per year and the like. Periodic longevity factor 112 includes a user identifier, which may include any of the user identifiers as described above.

With continued reference to FIG. 3, label generator module 108 retrieves a user periodic longevity factor training set 124 from a user database 128. User database 128 may include any data structure as described above. User periodic longevity factor training set 124 includes any of the user periodic longevity factor training set 124 as described above. User periodic longevity factor training set 124 includes a plurality of user data entries containing user periodic longevity data containing periodic longevity classification label 148. User periodic longevity factor training set 124 may include one or more periodic longevity factor 112 that were previously collected and stored within database 128. For instance and without limitation, user periodic longevity factor training set 124 may include twenty five data entries with each data entry containing a user periodic longevity factor 112 data containing a measurement reading of a user's blood pressure. In yet another non-limiting example, user periodic longevity factor training set 124 may include one hundred forty seven data entries with each data entry containing a user periodic longevity factor 112 data containing a user periodic longevity factor 112 data containing a user periodic longevity factor 112 data containing a measurement of beneficial and pathogenic bacteria located in a user's gut. In an embodiment, user periodic longevity factor training set 124 may include one or more periodic longevity factor 112 that may contain one or more different health measurements. For instance and without limitation, user periodic longevity factor training set 124 may include six data entries with a first data entry containing a periodic longevity factor 112 containing results from a CT scan of a user's head, a second data entry containing a periodic longevity factor 112 containing a chem-7 blood panel, a third data entry containing a periodic longevity factor 112 containing a chem-11 blood panel, a fourth data entry containing a periodic longevity factor 112 containing a microbiome analysis sample, a fifth data entry containing a periodic longevity factor 112 containing a blood pressure measurement, and a sixth data entry containing a periodic longevity factor 112 containing a hair sample analyzed for heavy metals. Selection of use data entries containing user periodic longevity data may be based on expert input, such as from expert database 140.

With continued reference to FIG. 3, label generator module 108 may retrieve a user periodic longevity factor training set 124 based on advisory input. Label generator module 108 may receive a periodic longevity selector input from an advisor client device 132. Periodic longevity selector input may include any of the periodic longevity selector inputs as described above in reference to FIG. 1. In an embodiment, a periodic longevity selector input may include an informed advisor's preference to select particular types of user periodic longevity data such as particular types or categories of health measurements. For instance and without limitation, a periodic longevity selector input may include an informed advisor's preference to utilize select user periodic longevity data pertaining to a user's gastrointestinal health include user data entries that contain stool samples analyzed for the absence or presence of harmful bacteria, methane breath tests, and blood tests analyzed for levels of digestive enzymes. Label generator module 108 may filter periodic longevity data containing periodic longevity classification label 148 based on a periodic longevity selector input. Filtering may include removing particular data entries from being contained within a particular user periodic longevity factor training set 124 or adding particular data entries to be contained within a particular user periodic longevity factor training set 124.

With continued reference to FIG. 3, label generator module 108 may include naïve Bayes classification module 304. Naïve Bayes classification module may be implemented as any hardware and/or software module. Naïve Bayes classification module may be configured to generate a naïve Bayes classification algorithm. Naïve Bayes classification algorithm includes any of the naïve Bayes classification algorithms as described above in reference to FIG. 1. Naïve Bayes classification algorithm utilizes a periodic longevity factor 112 as an input and outputs a periodic longevity classification label 148. Naïve Bayes classification module 204 generates a Naïve Bayes classification algorithm based on an assumption that each data entry contained within user periodic longevity factor training set 124 makes an independent and equal contribution to an outcome. Naïve Bayes classification module 304 generates naïve Bayes algorithm includes any mathematical formulas, calculations, and the like utilized to output a periodic longevity classification label 148. Periodic longevity classification label 148 may include any of the periodic longevity classification label 148 as described above. Naïve Bayes algorithm seeks to assign classification labels to problem instances which may be represented as vectors of feature values, and where classification labels may be drawn to a finite set. Naïve Bayes algorithm includes a series of calculations that assume the value of a particular data entry is independent of the value of any other feature, given a class variable. Naïve Bayes classification module 304 may be configured to calculate one or more variations of naïve Bayes algorithm including for example gaussian naïve Bayes, multinomial naïve Bayes, Bernoulli naïve Bayes, and/or semi-supervised parameter estimation. In an embodiment, naïve Bayes classification module 304 may select a particular naïve Bayes algorithm and/or series of calculations based on input contained within expert database 140.

Figure 4:
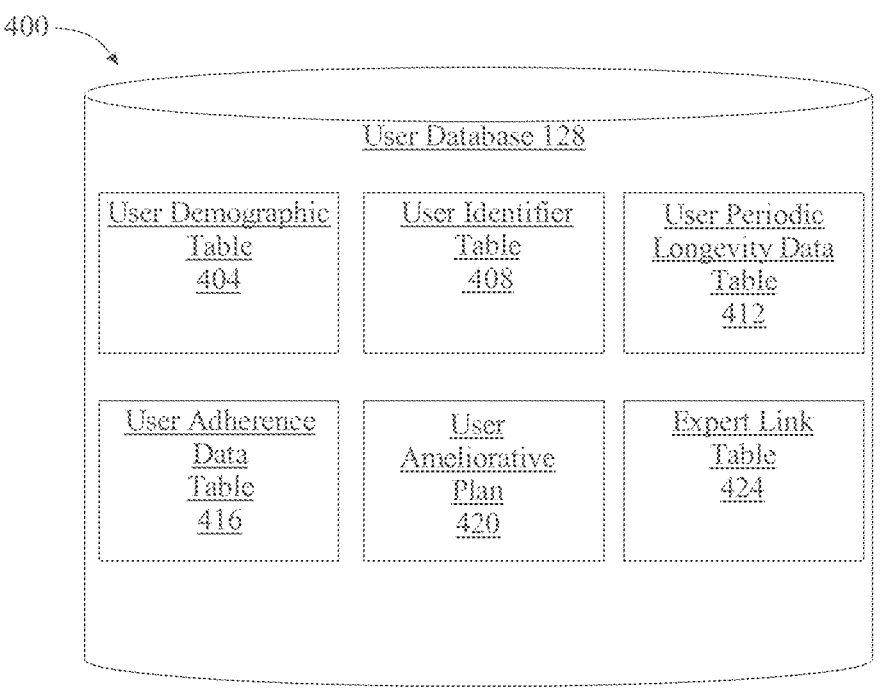
FIG. 4 is a block diagram illustrating an exemplary embodiment of a user database.

Referring now to FIG. 4, an exemplary embodiment 400 of user database 128 is illustrated. User database 128 may be implemented as any data structure as described above in reference to FIG. 1. One or more tables contained within user database 128 may include user demographic table 404; user demographic table 404 may include one or more data entries containing demographic information regarding a user. For instance and without limitation, user demographic table 404 may include information describing a user's full legal name, address, date of birth, education, income, occupation, marital status, family history, and the like. One or more tables contained within user database 128 may include user identifier table 408; user identifier table 408 may include one or more data entries containing one or more user identifiers. For instance and without limitation, user identifier table 408 may include a data entry containing a cryptographic public/private key pair uniquely assigned to a user. One or more tables contained within user database 128 may include user periodic longevity table 412; user periodic longevity table 412 may include one or more data entries containing user periodic longevity data. For instance and without limitation, user periodic longevity table 412 may include a plurality of user periodic longevity data including one or more measurements of a user's cholesterol panel, chem-7, heavy metal toxicity, gut function, gut wall integrity, environmental toxins, hormone panels, and the like. One or more tables contained within user database 128 may include user adherence data table 416; user adherence data table 416 may include one or more data entries containing user adherence data. For instance and without limitation, user adherence data table 416 may include one or more data entries containing a user's adherence such as how many times a user practiced a particular meditation sequence in the previous week. One or more tables contained within user database 128 may include user ameliorative plan 420; user ameliorative plan 420 may include one or more data entries containing one or more user ameliorative plan 180. For instance and without limitation, user ameliorative plan 420 may include one or more ameliorative plans generated by one or more informed advisors and/or machine-learning algorithms such as an ameliorative plan containing a yoga sequence for a user. One or more tables contained within user database 128 may include expert link table 424; expert link table 424 may include one or more data entries linking entries contained within user database 128 to one or more entries contained within expert database 140.

Figure 5:
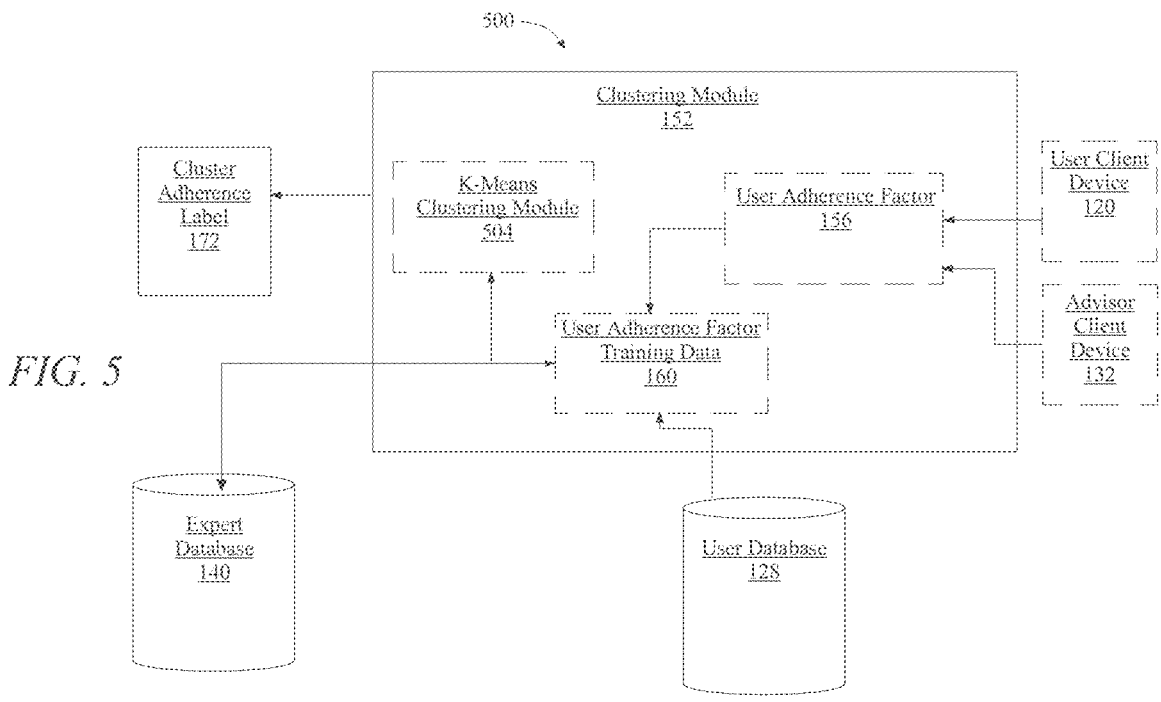
FIG. 5 is a block diagram illustrating an exemplary embodiment of a clustering module.

Referring now to FIG. 5, an exemplary embodiment 500 of clustering module 152 is illustrated. Clustering module 152 may be implemented as any hardware and/or software module. Clustering module 152 is configured to receive a user adherence factor 156 containing a user identifier from a user client device 120. A user adherence factor 156 includes any of the user adherence factor 156 as described above. For instance and without limitation, a user adherence factor 156 may include a description of how many times a user practiced a particular meditation sequence in the past week or a description of how many times a user complied with eating an anti-inflammatory diet in the past six weeks. User identifier includes any of the user identifiers as described above in reference to FIG. 1. In an embodiment, a user adherence factor 156 may be generated by an informed advisor on an advisor client device 132. For instance and without limitation, an informed advisor such as a user's functional medicine physician may generate a user adherence factor 156 after meeting for an appointment and discussing a user's progress with a particular ameliorative plan. In yet another non-limiting example, an informed advisor such as a user's massage therapist may generate a user adherence factor 156 after confirming that the user showed up for weekly massage sessions for three out of four weeks last month.

With continued reference to FIG. 5, clustering module 152 retrieves a user adherence factor training set 160 from user database 128 as a function of a user identifier. User adherence factor training set 160 includes any of the user adherence factor training set 160 as described above in reference to FIG. 1. User adherence factor training set 160 includes a plurality of unclassified user data entries containing user adherence data. Unclassified data entries include one or more data entries that have not been utilized in combination with one or more classification algorithms to generate one or more classification labels as described above. For instance and without limitation, user adherence data describing a user's completion of three Reiki sessions in six weeks that does not contain a classification label includes unclassified data. In yet another non-limiting example, user adherence data generated by an informed advisor such as user's yoga instructor may include a description of user's yoga attendance over the past year and may be stored within user database 128 without any classification labels. Clustering module 152 may retrieve a user adherence factor training set 160 containing a plurality of unclassified user data entries based on advisory input as to which unclassified user data entries should be utilized in user adherence factor training set 160. Clustering module 152 may receive an adherence factor selector input from an advisor client device 132. Adherence factor selector input may include input as to which unclassified user data entries should be utilized in a user adherence factor training set 160. For example, adherence factor selector input may include an advisor's recommendation to select user adherence data collected over a particular period of time, such as over the past two weeks. In yet another non-limiting example, adherence factor selector input may include an advisor's recommendation to select user adherence data that was generated in response to a particular ameliorative plan that was implemented, such as a plan to follow a fitness regimen or a plan to implement a yoga practice where user adherence data may reflect a user's adherence with the particular fitness regimen or with the yoga practice respectively. Clustering module 152 is configured to filter unclassified user data entries containing user adherence data based on an adherence factor selector input. Filtering may include selecting particular user data entries generated by a user and/or informed advisor that may be stored in user database 128 during particular dates, in response to particular ameliorative plans, generated from specific locations and the like. Filtering may include discarding particular user data entries generated by a user and/or informed advisor that may be stored in user database 128 that may not include data entries relevant to a particular ameliorative plan or that were collected outside of a particular time frame.

With continued reference to FIG. 5, clustering module 152 may include k-means clustering module 504. K-means clustering module 504 may be implemented as any hardware and/or software module. K-means clustering module 504 generates a k-means clustering algorithm using a user adherence factor training set 160. K-means clustering module 504 utilizes a user adherence factor 156 as an input and outputs a definite number of classified dataset clusters each containing cluster adherence label 172. "Cluster adherence label" as used in this disclosure, include descriptor uniquely identifying a particular dataset cluster. A "dataset cluster" as used in this disclosure, includes one or more data entries containing user adherence data. One or more data entries contained within a particular dataset cluster may contain a shared trait which may be reflected in a unique identifier of a particular dataset cluster. In an embodiment, a shared trait may include a particular level of adherence. For example. K-means clustering module 152 may generate a defined number of classified dataset clusters that each contain different levels of adherence. In such an instance, one or more data entries may be assigned to a particular dataset cluster based on the level of adherence contained within a particular data entry. Cluster adherence label 172 may be generated that uniquely identify level of adherence identified by a particular dataset cluster. For instance and without limitation, levels of adherence may include levels such as not adherent, mildly adherent, moderately adherent, mostly adherent, and very adherent. Levels of adherence may be generated based on expert input such as input received from expert database 140.

With continued reference to FIG. 5, K-means clustering module 504 may determine k-value that will set a fixed number of classified data entry cluster as outputs utilizing any of the methods as described above in reference to FIG. 1. In an embodiment, k-value may be selected based on expert input, such as input received from expert database 140. In an embodiment, k-value may be selected based upon generating a k-means clustering algorithm repeatedly until a k-value is averaged and selected. In yet another non-limiting example, a k-value may be selected based on a particular user adherence factor training set 160 that may be best suited for a particular k-value. K-means clustering module 404 receives as input user adherence factor training set 160 that contains a plurality of unclassified user data entries containing user adherence data. K-means clustering module 504 outputs a definite number of classified dataset clusters each containing cluster adherence label 172. Data entry clusters may be classified by K-means clustering module 504 using predictive modeling that approximates a mapping function from input variables to discrete output variables. Classification may be performed utilizing classification algorithms that include for example decision trees, naïve Bayes, artificial neural networks, boosting, kernel methods, and/or k-nearest neighbors algorithms. K-means clustering module 504 may generate a soft k-means clustering algorithm wherein a "soft k-means clustering algorithm" as used in this disclosure includes a k-means clustering algorithm where a cluster data entry may be selected and/or assigned to multiple clusters of the definite number of classified data entry clusters. For instance and without limitation, K-means clustering module 504 may generate a soft k-means clustering algorithm that has a k-value of seven and where a particular cluster data entry may be selected and assigned to three of the seven classified data entry clusters. K-means clustering algorithm module may generate a hard k-means clustering algorithm wherein a "hard k-means clustering algorithm" as used in this disclosure includes a k-means clustering algorithm where a cluster data entry may be selected to be assigned to one cluster of the definite number of classified data entry cluster. For instance and without limitation, K-means clustering module 504 may generate a hard k-means clustering algorithm that has a k-value of seven and where a particular cluster data entry may be selected and assigned to one of the seven classified data entry clusters. K-means clustering module 504 may select a hard k-means algorithm and/or a soft k-means algorithm based on expert input as described in more detail below. In an embodiment, K-means clustering module 504 may select a hard k-means algorithm and/or a soft k-means algorithm based on learned associations between clustering dataset and classified data entry outputs such as by learned associations.

Figure 6:
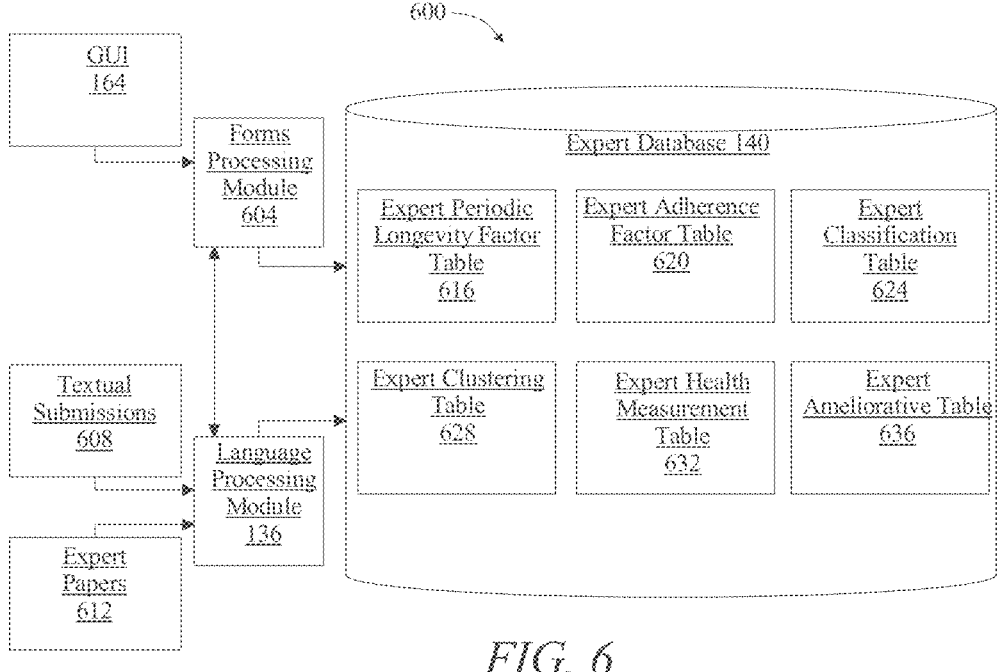
FIG. 6 is a block diagram illustrating an exemplary embodiment of an expert database.

Referring now to FIG. 6, an exemplary embodiment 600 of expert database 140 is illustrated. Expert database 140 may be implemented as any data structure suitable for use as user database 128 as described above. One or more database tables may be linked to one another by, for instance, common column values. For instance, a common column between two tables of expert database 140 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 6, expert database 140 includes a forms processing module 604 that may sort data entered in a submission via graphical user interface 164 by, for instance, sorting data from entries in the graphical user interface 164 to related categories of data; for instance, data entered in an entry relating in the graphical user interface 164 to a clustering algorithm may be sorted into variables and/or data structures for storage of clustering algorithms, while data entered in an entry relating to a category of training data and/or an element thereof may be sorted into variables and/or data structures for the storage of, respectively, categories of training data. Where data is chosen by an expert from pre-selected entries such as drop-down lists, data may be stored directly; where data is entered in textual form, language processing module 136 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 136 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 608, such as accomplished by filling out a paper or PDF form and/or submitting narrative information, may likewise be processed using language processing module 136. Data may be extracted from expert papers 512, which may include without limitation publications in medical and/or scientific journals, by language processing module 136 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 6, one or more tables contained within expert database 140 may include expert periodic longevity factor 112 table 616; expert periodic longevity factor 112 table 616 may include one or more data entries containing expert input regarding periodic longevity factor 112. One or more tables contained within expert database 140 may include expert adherence factor table 620; expert adherence factor table 620 may include one or more data entries containing expert input regarding adherence factors. One or more tables contained within expert database 140 may include expert classification table 624; expert classification table 624 may include one or more data entries containing expert input regarding classification labels and classification algorithms. One or more tables contained within expert database 140 may include expert clustering table 628; expert clustering table 628 may include one or more data entries containing expert input regarding clustering algorithms. One or more tables contained within expert database 140 may include expert health measurement table 632; expert health measurement table 632 may include one or more data entries containing expert input regarding health measurements. One or more tables contained within expert database 140 may include expert ameliorative table 636; expert ameliorative table 636 may include one or more data entries containing expert input regarding ameliorative plans and/or ameliorative processes.

Figure 7:
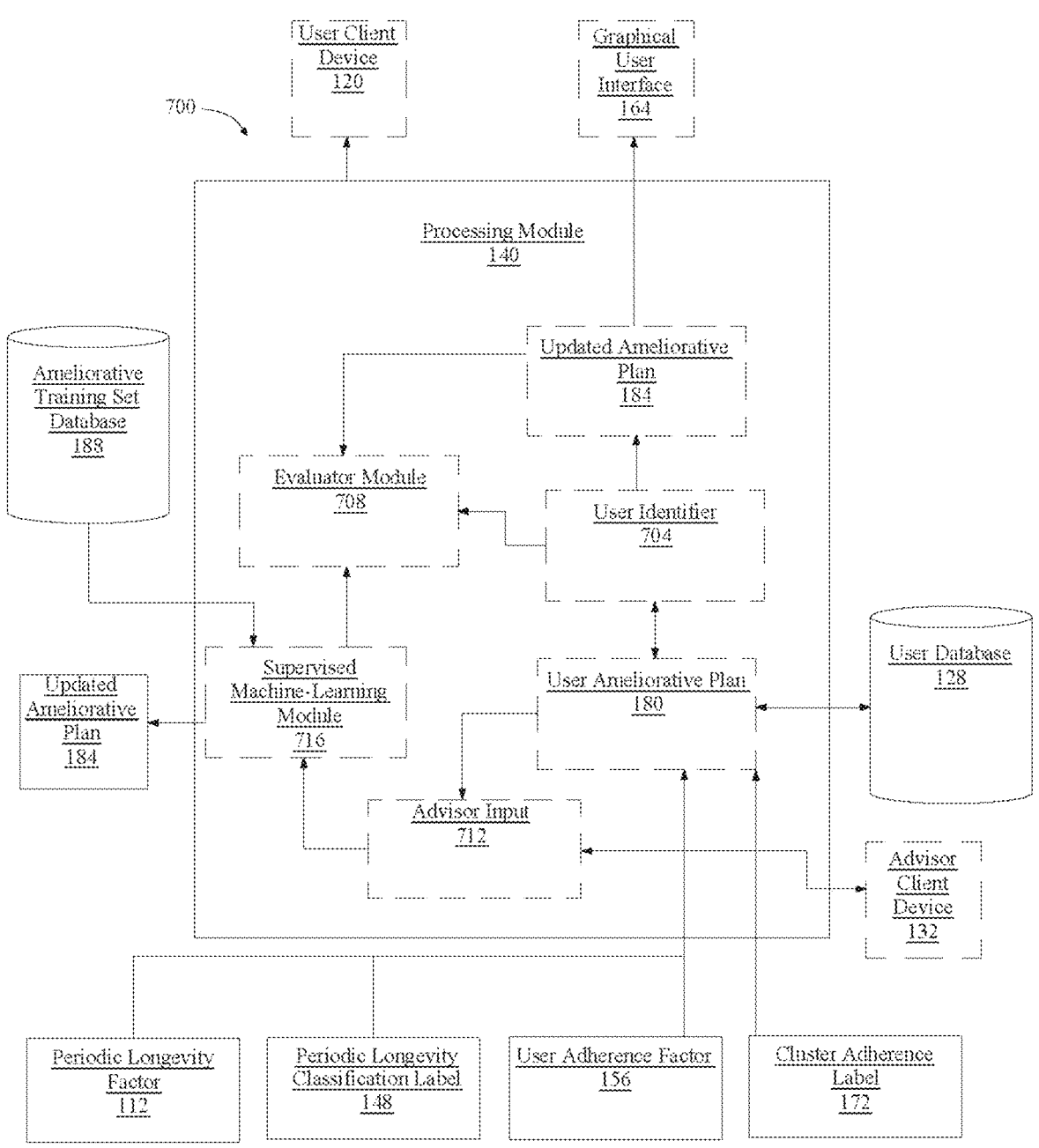
FIG. 7 is a block diagram illustrating an exemplary embodiment of a processing module.

Referring now to FIG. 7, an exemplary embodiment 700 of processing module 176 is illustrated. Processing module 176 may be implemented as any hardware and/or software module. Processing module 176 is configured to receive a periodic longevity factor 112 and a periodic longevity classification label 148 from the label generator module 108. This may be performed utilizing any network topography as described herein. Processing module 176 is configured to receive a user adherence factor 156 assigned to a particular classified dataset cluster containing a cluster adherence label 172. This may be performed utilizing any network topography as described herein. Processing module 176 retrieves a user ameliorative plan 180 from user database 128 as a function of a user identifier 704. User identifier 704 includes any of the user identifier 704 as described above in reference to FIG. 1. In an embodiment, processing module 176 may verify a user identifier 704 by matching a particular user identifier 704 contained within a periodic longevity factor 112 or a user adherence factor 156 to a user identifier 604 located within user database 128. For example, processing module 176 may evaluate a user's name and address to see if it matches a user's name and address contained within user database 128 or verify a public or private cryptographic key pair. Processing module 176 utilizes a user identifier 704 to retrieve a user ameliorative plan 180. User ameliorative plan 180 may include any of the user ameliorative plan 180 as described above in more detail. A user ameliorative plan 180 includes identification of one or more ameliorative processes. Ameliorative processes include any of the ameliorative processes as described above in reference to FIG. 1. For instance and without limitation, an ameliorative process may include a particular fitness regimen created for a user by an informed advisor. In yet another non-limiting example, an ameliorative plan may include one or more ameliorative processes such as implementation of an anti-inflammatory diet and initiation of a nightly meditation sequence.

With continued reference to FIG. 7, processing module 176 may include evaluator module 708. Evaluator module 708 may be implemented as any hardware and/or software module. Evaluator module 708 may be configured to evaluate a user ameliorative plan 180 utilizing a periodic longevity classification label 148 and a cluster adherence label 172. Evaluator module 708 may be configured to assess a periodic longevity factor 112 and a periodic longevity classification label 148 to determine if a periodic longevity classification label 148 contains an alert condition. An alert condition includes any situation when a periodic longevity factor 112 contains a health measurement that is outside of normal reference range limits or contains abnormal findings as described above in more detail in reference to FIG. 1. In an embodiment, evaluator module 708 may assess a periodic longevity classification label 148 to determine if the classification label suggests a possible alert condition. For instance and without limitation, evaluator module 708 may evaluate a periodic longevity classification label 148 to determine if a classification label contains a not normal label, an out of range label, an abnormal findings label, an unexpected results label and the like that indicates that a particular health measurement contained within a periodic longevity factor 112 is outside of normal limits or indicates an abnormal finding. In an embodiment, evaluator module 608 may evaluate a particular periodic longevity factor 112 to determine if it contains a value or finding that is outside of normal limits or that indicates abnormal results. Upon identification of an alert condition, evaluator module 708 displays a periodic longevity factor 112 and a periodic longevity classification containing the alert condition on a graphical user interface 164 located on a processor 104. Evaluator module 708 is configured to receive an advisory input 712 generated on a graphical user interface 164 located on a processor based on an alert condition. Advisory input 712 includes any feedback or response from an informed advisor as described above in more detail in reference to FIG. 1. For example, an informed advisor such as a functional medicine physician may generate an advisory input 712 that contains a description that the user needs to be seen for a follow up appointment with the informed advisor based on a particular health measurement contained within a periodic longevity factor 112 that indicates an alert condition. In yet another non-limiting example, an informed advisor who has a long standing relationship with a user may indicate that a particular alert condition is not something to take note of because the user routinely has a particular health measurement that is out of range due to another chronic illness or the like. In an embodiment, processing module 176 may utilize a particular advisory input 712 to generate an updated user ameliorative plan 184 as described in more detail below.

With continued reference to FIG. 7, evaluator module 708 may be configured to assess a user adherence factor 156 and a cluster adherence label 172 to determine if a cluster adherence label 172 contains a non-adherence label. Non-adherence label includes any cluster label that indicates non-adherence with a particular ameliorative plan as described above in more detail. Non-adherence label may include a spectrum of non-adherence such as labels that indicate mild adherence, minimum adherence, non-adherence and the like. Cluster adherence label 172 deemed to be considered non-adherent may be selected based on expert input such as input received from expert database 140. Upon identification of a non-adherent label, evaluator module 708 may display a user adherence factor 156 and a cluster adherence label 172 containing a non-adherence label on a graphical user interface 164 located on a processor 104. This may be displayed for an informed advisor, who may generate an advisory input 712 on the graphical user interface 164 located on the processor 104 based on the non-adherence label. Advisory input 712 may include any advisory input 712 as described above. In an embodiment, an advisory input 712 may include a recommendation that may be incorporated into an updated user ameliorative plan 184 such as a recommendation to adjust one or more ameliorative processes contained within an ameliorative plan based on an adherence factor. For example, a cluster adherence label 172 that contains a non-adherence label may be utilized by an informed advisor to scale back the intensity of a particular ameliorative process or select a different ameliorative process altogether.

With continued reference to FIG. 7, processing module 176 is configured to generate an updated user ameliorative plan 184. Processing module 176 may generate an updated user ameliorative plan 184 based on evaluating a periodic longevity classification label 148 and cluster adherence label 172. For example, periodic longevity classification label 148 that contain alert conditions may be utilized to scale back the intensity of one or more ameliorative processes or select a different ameliorative process all together. Periodic longevity classification label 148 that do not contain alert conditions may be utilized to increase the intensity of one or more ameliorative processes or to add in additional ameliorative processes. In yet another non-limiting example, non-adherence labels may be utilized to scale back the intensity of one or more ameliorative processes or to select a different ameliorative process all together. In yet another non-limiting example, cluster adherence label 172 that contain adherence labels may be utilized to increase the intensity of one or more ameliorative processes and to add on one or more ameliorative processes. Processing module 176 may evaluate periodic longevity classification label 148 and cluster adherence label 172 in combination. For example, a periodic longevity classification label 148 that indicates an alert condition in combination with a cluster adherence label 172 that indicates non-adherence may be utilized to generate an updated user ameliorative plan 184 that includes intervention by an informed advisor to determine why a user is not adhering to a particular ameliorative plan and why alert conditions are happening and if any other external factors may be negatively impacting a user's health. In such an instance, an updated user ameliorative plan 184 may be generated that includes a recommendation for behavior modification therapies to motivate a user to adhere to a particular ameliorative plan. In yet another non-limiting example, a periodic longevity classification label 148 that indicates an non-alert condition in combination with a cluster adherence label 172 that indicates adherence may be utilized to generate an updated user ameliorative plan 184 that maintains the same ameliorative process or adjusts it to slightly increase the intensity of the current ameliorative plan or to add on a second ameliorative process.

With continued reference to FIG. 7, generating an updated user ameliorative plan 184 may include receiving advisory input 712 by processing module 176. Processing module 176 may display a periodic longevity classification label 148 and a cluster adherence label 172 on a graphical user interface 164 located on a processor 104. Processing module 176 may receive an advisory input 712 generated by an informed advisor on a graphical user interface 164 located on a processor. Processing module 176 may generate an updated user ameliorative plan 184 based on the advisory input 712. For instance and without limitation, an advisory input 712 may include a recommendation to eliminate a particular ameliorative process contained within an ameliorative plan and instead to select a separate ameliorative process that may take less time each day for a user to implement because a user has been non-adherent with a particular ameliorative plan. In yet another non-limiting example, a particular user periodic longevity factor 112 that continues to contain alert conditions such as elevated blood glucose levels, may cause an informed advisor to generate an updated user ameliorative plan 184 that includes a recommendation to initiate a second supplement to decrease elevated blood glucose levels as well as initiating a second ameliorative process that includes a recommendation to initiate a high intensity interval fitness regimen.

With continued reference to FIG. 7, processing module 176 may include supervised machine-learning module 716. Supervised machine-learning module 716 may be implemented as any hardware and/or software module. Supervised machine-learning module 716 may be utilized to generate an updated user ameliorative plan 184. Supervised machine-learning module 716 generates an updated user ameliorative plan 184 by generating an ameliorative model. Ameliorative model may include any machine-learning process that may include linear or polynomial regression algorithms, may include calculating one or more equations, may include a set of instructions to generate outputs based on inputs which may be derived using any machine-learning algorithm and the like. Supervised machine-learning module 716 selects ameliorative training set from an ameliorative training set database 188. Ameliorative training set database 188 may include any data structure suitable for use as user database 128 as described above. Ameliorative training set includes a plurality of data entries containing a first ameliorative plan containing a periodic longevity classification label 148 and a cluster adherence label 172 correlated to a second ameliorative plan. Ameliorative training set may include any of the training data as described above in reference to FIG. 1. For instance and without limitation, ameliorative training set may include a plurality of data entries containing a first ameliorative plan containing a periodic longevity classification containing a not normal classification label and a cluster adherence label 172 containing a mildly adherent label correlated to a second ameliorative plan. Supervised machine-learning module 716 may select ameliorative training set from ameliorative training set database 188 utilizing a periodic longevity classification label 148 and a cluster adherence label 172. Ameliorative training sets contained within ameliorative training set database 188 may be organized according to particular classification labels that may be matched to periodic classification labels and cluster adherence label 172. For instance and without limitation, a periodic classification label that contains a classification label such as normal range may be matched to an ameliorative training set contained within ameliorative training set database 188 that contains a classification label that contains a normal range classification label. In yet another non-limiting example, a cluster adherence label 172 that contains a moderately adherent label may be matched to an ameliorative training set contained within ameliorative training set database 188 that contains a moderately adherent label. Supervised machine-learning module 716 generates using a supervised machine-learning algorithm an ameliorative model that outputs an updated user ameliorative plan 184 utilizing the ameliorative training set. Supervised machine-learning algorithm includes any of the supervised machine-learning algorithms as described above in reference to FIG. 1. Supervised machine-learning algorithm outputs an updated user ameliorative plan 184 utilizing the ameliorative training set.

Figure 8:
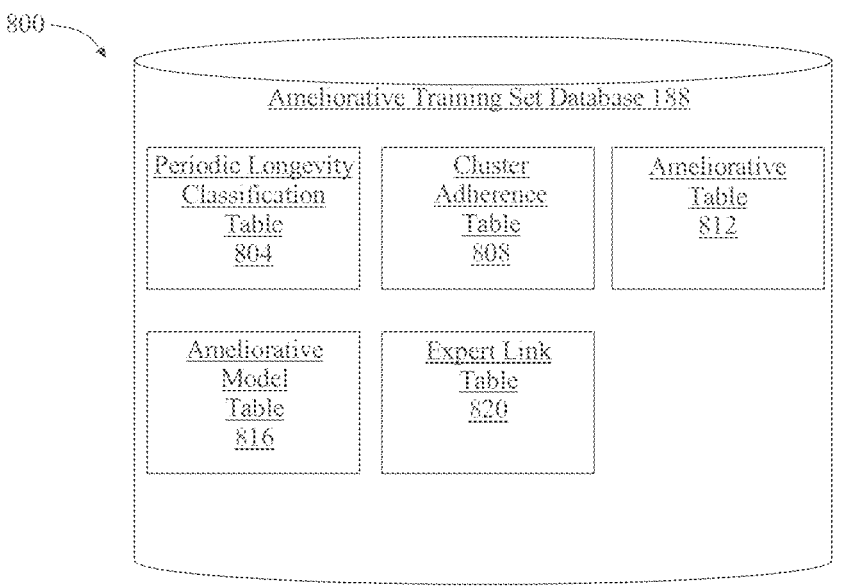
FIG. 8 is a block diagram illustrating an exemplary embodiment of an ameliorative training set database.

Referring now to FIG. 8, an exemplary embodiment of ameliorative training set database 188 is illustrated. Ameliorative training set database 188 may be implemented as any data structure suitable for use as user database 128 as described above in more detail in reference to FIG. 1. One or more tables contained within ameliorative training database 188 may include periodic longevity classification table 804; periodic longevity classification table 804 may include one or more data entries containing ameliorative training sets organized by periodic longevity classification label 148. One or more tables contained within ameliorative training set database 188 may include cluster adherence table 808; cluster adherence table 808 may include one or more data entries containing ameliorative training sets organized by cluster adherence label 172. One or more tables contained within ameliorative training set database 188 may include ameliorative table 712; ameliorative table 812 may include one or more ameliorative training sets organized by ameliorative plans and/or ameliorative processes. One or more tables contained within ameliorative training set database 188 may include ameliorative model table 816; ameliorative model table 816 may include one or more ameliorative models that may be selected by processing module 176 and/or supervised machine-learning module to generate a supervised machine-learning algorithm. One or more tables contained within ameliorative training set database 188 may include expert link table 820; expert link table 820 may include one or more data entries linking entries contained within ameliorative training set database 188 to one or more entries contained within expert database 140.

Figure 9:
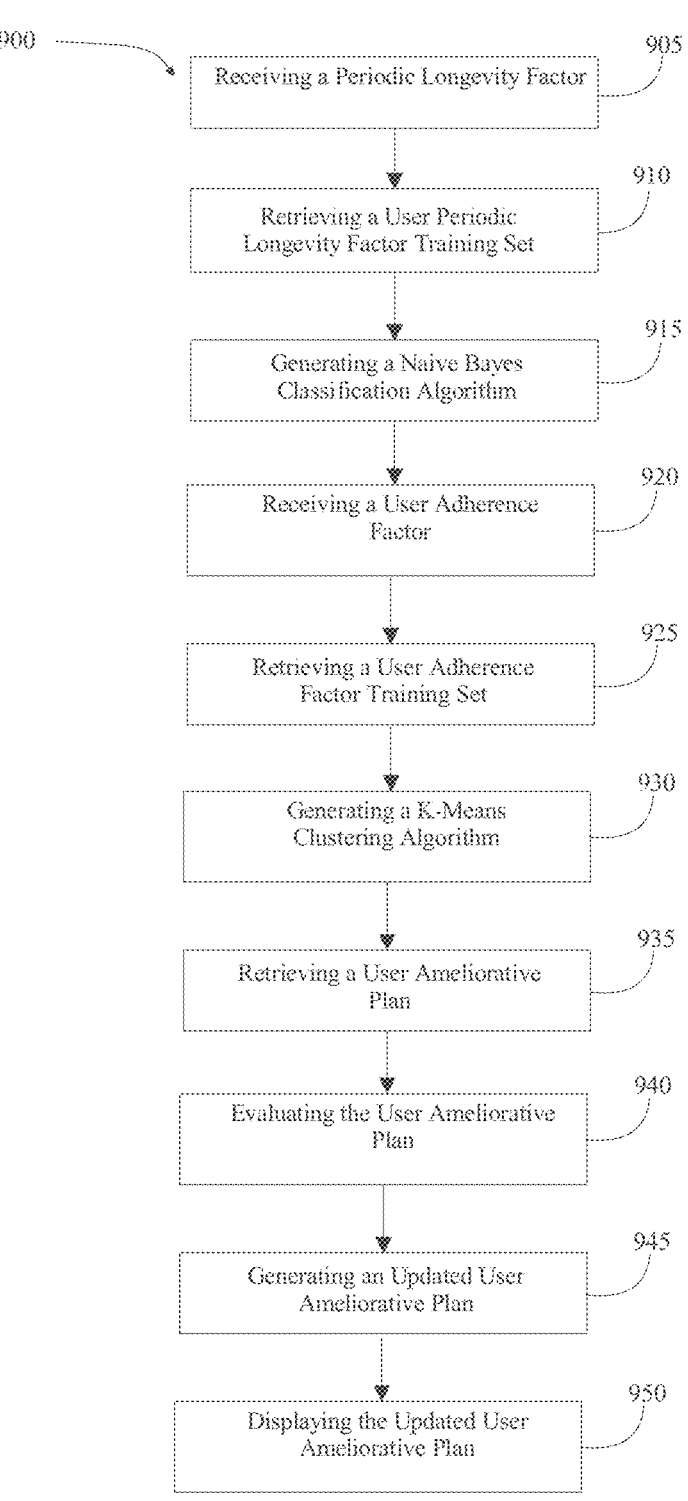
FIG. 9 is a process flow diagram illustrating an exemplary embodiment of a method of providing dynamic constitutional guidance.

Referring now to FIG. 9, an exemplary embodiment of a method 900 of providing dynamic constitutional guidance is illustrated. At step 905 a processor receives a periodic longevity factor 112 containing a user identifier from a user client device 120. A processor may receive a periodic longevity factor 112 utilizing any of the network methodologies as described herein. A periodic longevity factor 112 includes any of the periodic longevity factor 112 as described above in reference to FIGS. 1-8. For example, a periodic longevity factor 112 may include any health measurement such as a measurement of a user's heart rate or a medical scan of a user's ankle joint. A processor 104 may receive a periodic longevity factor 112 periodically which includes receiving at least a health measurement at intervals where intervals indicate a particular passage of time. For example, a processor 104 may receive a periodic longevity factor 112 such as a heart rate measurement every minute while a processor 104 may receive a periodic longevity factor 112 such as an electroencephalogram every three months. A periodic longevity factor 112 may be received by a processor 104 and stored in user database 128. User identifier includes any of the user identifiers as described above in reference to FIGS. 1-8. User client device 120 includes any of the user client device 120 as described above in reference to FIGS. 1-8.

With continued reference to FIG. 9, at step 910 a processor 104 retrieves a user periodic longevity factor training set 124 from a user database 128 as a function of a user identifier wherein a user periodic longevity factor training set 124 contains a plurality of user data entries containing user periodic longevity data containing periodic longevity classification label 148. A processor may retrieve a user periodic factor training set from a user database 128 by matching a user identifier to a stored user identifier contained within user database 128 as described above in more detail in reference to FIGS. 1-8. User periodic factor training set includes any of the user periodic factor training sets as described above in reference to FIGS. 1-8. Periodic factor training set may include a plurality of user data entries containing user periodic longevity data. User periodic longevity data selected to be included within periodic factor training set may be selected based on input from an informed advisor. At least a processor may receive a periodic longevity selector input from an advisor client device 132. Periodic longevity selector input includes any of the periodic longevity selector inputs as described above in reference to FIGS. 1-8. For example, a periodic longevity selector input may include an informed advisor's input to select user data entries received by a processor during a particular period of time such as when an ameliorative process is first initiated or later when an ameliorative process has been implemented by a user for a particular length of time. A processor 104 may filter user periodic longevity data stored within user database 128 based on a periodic longevity selector input. For example, a processor 104 may select user periodic longevity data that may be dated for a particular time period and disregard other user periodic longevity data that may not be dated for the particular time period contained within a periodic longevity selector input. A processor 104 retrieves user periodic longevity factor 112 training data from a user database 128 that contains periodic longevity classification label 148. Periodic longevity classification label 148 include any of the periodic longevity classification label 148 as described above in reference to FIGS. 1-8. User periodic longevity factor 112 training data that contains user periodic longevity data containing periodic longevity classification label 148 may contain periodic longevity classification label 148 previously generated by a processor 104 utilizing any of the classification algorithms as described herein.

With continued reference to FIG. 9, at step 915 a processor 104 generates a naïve Bayes classification algorithm utilizing the user periodic longevity factor training set 124 wherein the naïve Bayes classification algorithm utilizes the periodic longevity factor 112 as an input and outputs a periodic longevity classification label 148. Naïve Bayes classification algorithm includes any of the Naïve Bayes classification algorithms as described above in reference to FIGS. 1-8. A processor may generate a Naïve Bayes classification algorithm utilizing any of the methods as described above in reference to FIGS. 1-8.

With continued reference to FIG. 9, at step 920 a processor 104 receives a user adherence factor 156 containing a user identifier from a user client device 120. A processor 104 receives a user adherence factor 156 utilizing any network methodology as described herein. A user adherence factor 156 includes any of the user adherence factor 156 as described above in reference to FIGS. 1-8. For example, a user adherence factor 156 may include a description of how many times a user implemented a particular ameliorative process over the course of the previous week. A user adherence factor 156 may be generated by a user from a user client device 120. User client device 120 includes any of the user client device 120 as described above in more detail in reference to FIGS. 1-8. User adherence factor 156 contains a user identifier which may include any of the user identifiers as described above. A user adherence factor 156 containing a user identifier may be generated on a graphical user interface 164 located on a processor by an informed advisor. For example, a user's health coach may generate a user adherence factor 156 describing how many sessions the user completed over the previous six months.

With continued reference to FIG. 9, at step 925 a processor 104 retrieves a user adherence factor training set 160 from a user database 128 as a function of a user identifier wherein the user adherence factor training set 160 contains a plurality of unclassified user data entries containing user adherence data. User adherence factor training set 160 includes any of the user adherence factor training set 160 as described above in reference to FIGS. 1-8. User adherence factor training set 160 includes a plurality of unclassified user data entries containing user adherence data. User adherence data selected to be included within user adherence factor training set 160 may be selected based on input from an informed advisor. At least a processor may receive an adherence factor selector input from an advisor client device 132. Adherence factor selector input includes any of the adherence factor selector inputs as described above in reference to FIGS. 1-8. For example, an adherence factor selector input may include an informed advisor's input to select user data entries received by a processor during a particular period of time such as when a user is noncompliant or when a user actively adheres to a particular ameliorative plan. A processor 104 may filter unclassified data entries stored within user database 128 based on an adherence factor selector input. For example, a processor 104 may select user unclassified data entries that were collected during a particular period of time such as when a user first initiated an ameliorative process or a processor 104 may select user unclassified data entries that were generated by an informed advisor and not by the user.

With continued reference to FIG. 9, at step 930 a processor generates a k-means clustering algorithm using the user adherence factor training set 160 wherein the k-means clustering algorithm utilizes the user adherence factor 156 as an input and outputs a definite number of classified dataset clusters each containing cluster adherence label 172 wherein the user adherence factor 156 is assigned to a particular classified dataset cluster containing a cluster adherence label 172 as a function of generating the k-means clustering algorithm. A processor 104 may generate a k-means clustering algorithm utilizing any of the methods as described above in reference to FIGS. 1-7. A processor 104 may output a definite number of classified dataset clusters based on input from expert database 140 as described above.

With continued reference to FIG. 9, at step 935 a processor 104 retrieves a user ameliorative plan 180 from a user database 128 as a function of a user identifier wherein the user ameliorative plan 180 contains at least an ameliorative process. A processor 104 may retrieve a user ameliorative plan 180 by matching a user identifier to a user identifier contained within a user database 128. For example, a processor 104 may match a username and date of birth to a username and date of birth contained within user database 128.

With continued reference to FIG. 9, at step 940 a processor 104 evaluates a user ameliorative plan 180 as a function of a periodic longevity classification label 148 and a cluster adherence label 172. A processor 104 may evaluate a user ameliorative plan 180 utilizing any of the methods as described above in reference to FIGS. 1-8. Evaluating a user ameliorative plan 180 may include assessing the periodic longevity factor 112 and the periodic longevity classification label 148 to determine that the periodic longevity classification label 148 contains an alert condition; displaying the periodic longevity factor 112 and the periodic longevity classification label 148 containing the alert condition on the graphical user interface 164 located on the processor; and receiving an advisory input generated on the graphical user interface 164 located on the processor as a function of the alert condition. This may be performed utilizing any of the methods as described above in reference to FIGS. 1-8. Evaluating a user ameliorative plan 180 may include assessing the user adherence factor 156 and the cluster adherence label 172 to determine that the cluster adherence label 172 contains a non-adherence label; displaying the user adherence factor 156 and the cluster adherence label 172 containing the non-adherence label on a graphical user interface 164 located on the processor; and receiving an advisory input generated on the graphical user interface 164 located on the processor as a function of the non-adherence label. This may be performed utilizing any of the methods as described above in reference to FIGS. 1-8.

With continued reference to FIG. 9, at step 945 a processor 104 generates an updated user ameliorative plan 184 as a function of evaluating a user ameliorative plan 180. Updated user ameliorative plan 184 may include any of the updated user ameliorative plan 184 as described above in reference to FIGS. 1-8. For example, an updated user ameliorative plan 184 may include a change to one or more ameliorative processes contained within an ameliorative plan. A processor 104 generates an updated user ameliorative plan 184 based on advisory input. A processor 104 generates an updated user ameliorative plan 184 by displaying the periodic longevity classification label 148 and the cluster adherence label 172 on a graphical user interface 164 located on the processor; receiving an advisory input generated by an informed advisor on the graphical user interface 164 located on the processor; and generating an updated user ameliorative plan 184 as a function of the advisory input.

For example, an advisory input may include a recommendation to decrease the frequency that a user practices a particular fitness routine and an ameliorative plan may be updated to decrease the frequency of the particular fitness plan.

With continued reference to FIG. 9, generating an updated user ameliorative plan 184 may include generating one or more supervised machine-learning algorithms. A processor 104 may select ameliorative training set from a ameliorative training set database 188 as a function of the periodic longevity classification label 148 and the cluster adherence label 172 and wherein the ameliorative training set includes a plurality of data entries containing a first ameliorative plan containing a periodic longevity classification label 148 and a cluster adherence label 172 correlated to a second ameliorative plan; and generate using a supervised machine-learning algorithm an ameliorative model that outputs an updated user ameliorative plan 184 utilizing the ameliorative training set. This may be performed utilizing any of the methods as described above in reference to FIGS. 1-8. Generating an updated user ameliorative plan 184 may include transmitting a response for more data to a user client device. Processor 104 may transmit to a user client device a request for one or more additional periodic longevity factors, such as when an informed advisor may request more real time data in an advisory input. Processor 104 may transmit to a user client device a request for one or more additional user adherence factors such as when an informed advisor may request one or more additional user adherence factors.

With continued reference to FIG. 9, at step 950 a processor 104 displays an updated user ameliorative plan 184 on a graphical user interface 164 located on a processor 104. A processor 104 may display an updated user ameliorative plan 184 utilizing any of the methods as described herein.

Figure 10:
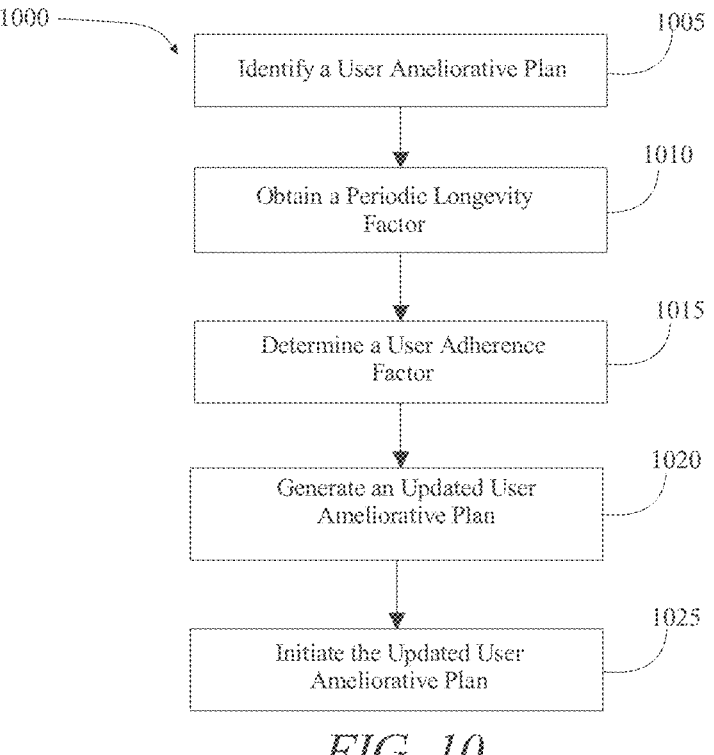
FIG. 10 is a process flow diagram illustrating an exemplary embodiment of a method for initiating an updated ameliorative plan.

Now Referring to FIG. 10, at step 1005, a processor 104 identifies a user ameliorative plan 180. User ameliorative plan 180 includes any of the user ameliorative plan 180 as described above, in reference to FIGS. 1-9. Processor 104 identifies user ameliorative plan 180 as a function of a user identifier 204 from a user client device 120. User identifier 204 includes any of the user identifier 204 as described above, in reference to FIGS. 1-9. User client device 120 includes any of the user client device 120 as described above, in reference to FIGS. 1-9.

Still referring to FIG. 10, at step 1010, processor 104 obtains a periodic longevity factor 112. Periodic longevity factor 112 includes any of the periodic longevity factor 112 as described above, in reference to FIGS. 1-9.

Still referring to FIG. 10, at step 1015, processor 104 determines a user adherence factor 156. User adherence factor 156 includes any of the user adherence factor 156 as described above, in reference to FIGS. 1-9. Processor 104 identifies a progression locus 208 as a function of user ameliorative plan 180 and periodic longevity factor 112. Progression locus 208 includes any of the progression locus 208 as described above, in reference to FIGS. 1-9. Processor 104 receives a user response 212. User response 212 includes any of the user response 212 as described above, in reference to FIGS. 1-9. Processor 104 determines user adherence factor 156 as a function of progression locus 208 and user response 212, wherein determining is performed according to any of the determining as described above, in reference to FIGS. 1-9.

Still referring to FIG. 10, at step 1020, processor 104 generates an updated user ameliorative plan 184 as a function of user adherence factor 156. Updated user ameliorative plan 184 includes any of the updated user ameliorative plan 184 as described above, in reference to FIGS. 1-9.

Still referring to FIG. 10, at step 1025, processor 104 initiates updated user ameliorative plan 184. Initiating may include any of the initiating as described above, in reference to FIGS. 1-9.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
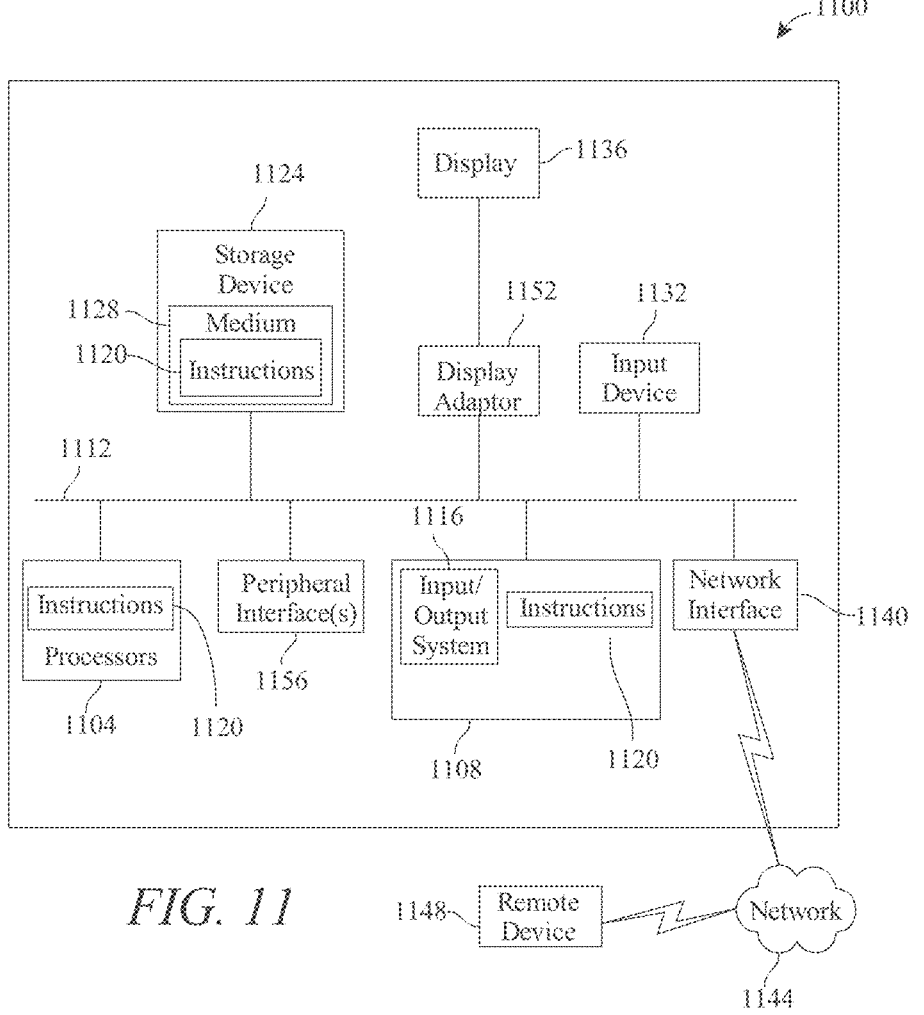
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Memory 1108 may include various components (e.g., machine-readable media) including, but not limited to, a random access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIRE-WIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for initiating an updated user ameliorative plan the system comprising:
a processor, wherein the processor is configured to:
identify a user ameliorative plan as a function of a user identifier from a user client device;
obtain a periodic longevity factor;
generate a user adherence factor using an informed advisor, wherein generating the user adherence factor comprises:
receiving, using a graphical user interface, a spoken command from the informed advisor;
converting, using the processor, the spoken command into a textual output;
displaying, using the graphical user interface, the textual output;
identify a progression locus as a function of the user ameliorative plan and the periodic longevity factor;
determine the user adherence factor as a function of the progression locus, wherein determining the user adherence factor further comprises:
receiving an adherence training set correlating a plurality of progression locus and a plurality of user responses to adherence factors;
training an adherence machine-learning model, wherein the adherence machine-learning model is trained as a function of the adherence training set, and wherein the training includes applying domain restrictions to the adherence training set to remove artifacts in the adherence training set to improve an accuracy of the adherence machine-learning model; and
determining the user adherence factor as a function of the adherence machine-learning model;
generate an updated user ameliorative plan as a function of the user adherence factor; and
initiate the updated user ameliorative plan.

2. The system of claim 1, wherein obtaining the periodic longevity factor further comprises receiving at least a health measurement as a function of a sensor.

3. The system of claim 1, wherein obtaining the periodic longevity factor further comprises receiving an informed advisor input.

4. The system of claim 1, wherein identifying the progression locus further comprises:
determining a buffer zone as a function of the user ameliorative plan; and
identifying the progression locus as a function of the buffer zone and the periodic longevity factor.

5. The system of claim 1, wherein generating the updated user ameliorative plan further comprises:
identifying an optimized user adherence factor; and
generating the updated user ameliorative plan as a function of the optimized user adherence factor.

6. The system of claim 5, wherein identifying the optimized user adherence factor further comprises determining a modification element and identifying the optimized user adherence factor as a function of the modification element.

7. The system of claim 1, wherein initiating the updated user ameliorative plan further comprises transmitting the updated user ameliorative plan to the user client device.

8. The system of claim 1, wherein determining the user adherence factor further comprises identifying a compliance element.

9. The system of claim 1, wherein generating the user adherence factor further comprises receiving a user response, wherein the user response further comprises identifying a routine element.

10. A method for initiating an updated user ameliorative plan the method comprising:

identifying, by a processor, a user ameliorative plan as a function of a user identifier from a user client device;

obtaining, by the processor, a periodic longevity factor;

generating, by the processor, a user adherence factor using an informed advisor, wherein generating the user adherence factor comprises:

receiving, using a graphical user interface, a spoken command from the informed advisor;

converting, using the processor, the spoken command into a textual output;

displaying, using the graphical user interface, the textual output;

identifying, by the processor, a progression locus as a function of the user ameliorative plan and the periodic longevity factor;

determining, by the processor, the user adherence factor as a function of the progression locus, wherein determining the user adherence factor further comprises:

receiving an adherence training set correlating a plurality of progression locus and a plurality of user responses to adherence factors;

training an adherence training set correlating a plurality of progression locus and a plurality of user responses to adherence factors;

training an adherence machine-learning model, wherein the adherence machine-learning model is trained as a function of the adherence training set, and wherein the training includes applying domain restrictions to the adherence training set to remove artifacts in the adherence training set to improve an accuracy of the adherence machine-learning model; and determining the user adherence factor as a function of the adherence machine-learning model;

generating, by the processor, an updated user ameliorative plan as a function of the user adherence factor; and initiating, by the processor, the updated user ameliorative plan.

11. The method of claim 10, wherein obtaining the periodic longevity factor further comprises receiving at least a health measurement as a function of a sensor.

12. The method of claim 10, wherein obtaining the periodic longevity factor further comprises receiving an informed advisor input.

13. The method of claim 10, wherein identifying the progression locus further comprises:

determining a buffer zone as a function of the user ameliorative plan; and identifying the progression locus as a function of the buffer zone and the periodic longevity factor.

14. The method of claim 11, wherein generating the updated user ameliorative plan further comprises:

identifying an optimized user adherence factor; and generating the updated user ameliorative plan as a function of the optimized user adherence factor.

15. The method of claim 14, wherein identifying the optimized user adherence factor further comprises determining a modification element and identifying the optimized user adherence factor as a function of the modification element.

16. The method of claim 10, wherein initiating the updated user ameliorative plan further comprises transmitting the updated user ameliorative plan to the user client device.

17. The method of claim 10, wherein determining the user adherence factor further comprises identifying a compliance element.

18. The method of claim 10, wherein generating the user adherence factor further comprises receiving a user response, wherein the user response further comprises identifying a routine element.

* * * * *